(12) United States Patent
Kumar et al.

(10) Patent No.: US 8,710,266 B2
(45) Date of Patent: *Apr. 29, 2014

(54) NITROGEN AND HINDERED PHENOL CONTAINING DUAL FUNCTIONAL MACROMOLECULAR ANTIOXIDANTS: SYNTHESIS, PERFORMANCES AND APPLICATIONS

(75) Inventors: Rajesh Kumar, Dracut, MA (US); Suizhou Yang, Lowell, MA (US); Vijayendra Kumar, Dracut, MA (US); Ashok L. Cholli, Chelmsford, MA (US)

(73) Assignee: Polnox Corporation, Lowell, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/298,948

(22) Filed: Nov. 17, 2011

(65) Prior Publication Data

US 2012/0142968 A1 Jun. 7, 2012

Related U.S. Application Data

(60) Continuation of application No. 12/854,347, filed on Aug. 11, 2010, now Pat. No. 8,080,689, which is a division of application No. 11/360,020, filed on Feb. 22, 2006, now Pat. No. 7,799,948.

(60) Provisional application No. 60/555,169, filed on Feb. 22, 2005.

(51) Int. Cl.
*C07C 211/00* (2006.01)
*C08F 8/32* (2006.01)
*C10M 159/12* (2006.01)

(52) U.S. Cl.
USPC .......................................... 564/307; 508/543

(58) Field of Classification Search
None
See application file for complete search history.

(56) References Cited

U.S. PATENT DOCUMENTS

| | | |
|---|---|---|
| 3,116,305 A | 12/1963 | Morris et al. |
| 3,294,836 A | 12/1966 | Peterson et al. |
| 3,441,545 A | 4/1969 | Blatz et al. |
| 3,459,704 A | 8/1969 | Peterson et al. |
| 3,557,245 A | 1/1971 | Phillips et al. |
| 3,632,785 A | 1/1972 | Bornstein |
| 3,645,970 A | 2/1972 | Kleiner |
| 3,649,667 A | 3/1972 | Song et al. |
| 3,655,831 A | 4/1972 | Friedman |
| 3,870,680 A | 3/1975 | Schurdak |
| 3,907,939 A | 9/1975 | Robin et al. |
| 3,953,402 A | 4/1976 | Kline |
| 3,965,039 A | 6/1976 | Chaplits et al. |
| 3,983,091 A | 9/1976 | Gloth et al. |
| 3,994,828 A | 11/1976 | Zaffaroni |
| 3,996,160 A | 12/1976 | Dale et al. |
| 3,996,198 A | 12/1976 | Wang et al. |
| 4,054,676 A | 10/1977 | Weinshenker et al. |
| 4,094,857 A | 6/1978 | Wolfe, Jr. |
| 4,096,319 A | 6/1978 | Willette et al. |
| 4,097,464 A | 6/1978 | Kline |
| 4,098,829 A | 7/1978 | Weinshenker et al. |
| 4,107,144 A | 8/1978 | Russell et al. |
| 4,136,055 A | 1/1979 | Lyons |
| 4,202,816 A | 5/1980 | Moser et al. |
| 4,205,151 A | 5/1980 | Dale et al. |
| 4,213,892 A | 7/1980 | Scott |
| 4,219,453 A | 8/1980 | Sakurai et al. |
| 4,267,358 A | 5/1981 | Hechenbleikner et al. |
| 4,281,192 A | 7/1981 | Jacquet et al. |
| 4,283,572 A | 8/1981 | Klicker |
| 4,317,933 A | 3/1982 | Parker |
| 4,341,879 A | 7/1982 | Sugio et al. |
| 4,355,148 A | 10/1982 | Layer et al. |
| 4,377,666 A | 3/1983 | Farrar |
| 4,380,554 A | 4/1983 | Serres, Jr. |
| 4,447,657 A | 5/1984 | Firth et al. |
| 4,465,871 A | 8/1984 | Firth et al. |
| 4,510,296 A | 4/1985 | Hergenrother |
| 4,511,491 A | 4/1985 | Ishii et al. |
| 4,634,728 A | 1/1987 | Dunski et al. |
| 4,690,995 A | 9/1987 | Keskey et al. |
| 4,761,247 A | 8/1988 | Rei et al. |
| 4,824,929 A | 4/1989 | Arimatsu et al. |
| 4,849,503 A | 7/1989 | Cotter et al. |

(Continued)

FOREIGN PATENT DOCUMENTS

| | | |
|---|---|---|
| CS | 111291 | 6/1964 |
| DE | 197 47 644 A1 | 5/1999 |

(Continued)

OTHER PUBLICATIONS http://www.machinerylubrication.com/Read/1028/oxidation-lubricant (Mar. 29, 2010, pp. 1-7).*
Akkara, J.A., et al., "Hematin-Catalyzed Polymerization of Phenol Compounds," Macromolecules, 33(7):2377-2382 (2000).
Akkara, J.A., et al., "Synthesis and Characterization of Polymers Produced by Horseradish Peroxidase in Dioxane," *J. of Polymer Science: Part A: Polymer Chemistry*, 29(11):1561-1574 (1991).
Armengol, E., et al., "Acid Zeolites as Catalysts in Organic Reactions, tert-Butylation of Anthracene, Naphthalene and Thianthrene," *Appl. Catal. A* 149:411-423 (1997).

(Continued)

*Primary Examiner* — Clinton Brooks
(74) *Attorney, Agent, or Firm* — Hamilton, Brook, Smith & Reynolds, P.C.

(57) ABSTRACT

Disclosed are compounds represented by structural formula (I):

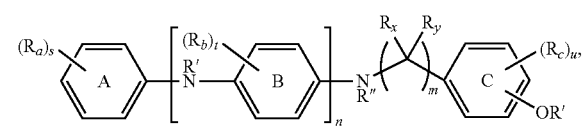

methods of producing compounds represented by structural formula (I). and their use in inhibiting oxidation in an oxidizable material.

11 Claims, 3 Drawing Sheets

(56) References Cited

U.S. PATENT DOCUMENTS

| | | |
|---|---|---|
| 4,855,345 A | 8/1989 | Rosenberger et al. |
| 4,857,596 A | 8/1989 | MacLeay et al. |
| 4,870,214 A | 9/1989 | Mina et al. |
| 4,894,263 A | 1/1990 | Dubois et al. |
| 4,897,438 A | 1/1990 | Kikuchi et al. |
| 4,900,671 A | 2/1990 | Pokora et al. |
| 4,925,591 A | 5/1990 | Nakauchi et al. |
| 4,968,759 A | 11/1990 | Kikuchi et al. |
| 4,977,004 A | 12/1990 | Bettle, III et al. |
| 4,981,917 A | 1/1991 | MacLeay et al. |
| 4,994,628 A | 2/1991 | Goddard et al. |
| 5,013,470 A | 5/1991 | Benfaremo |
| 5,017,727 A | 5/1991 | Olivier |
| 5,082,358 A | 1/1992 | Tabata et al. |
| 5,102,962 A | 4/1992 | Kikuchi et al. |
| 5,117,063 A | 5/1992 | Stern et al. |
| 5,143,828 A | 9/1992 | Akkara et al. |
| 5,155,153 A | 10/1992 | Neri et al. |
| 5,185,391 A | 2/1993 | Stokich, Jr. |
| 5,185,407 A | 2/1993 | Wong |
| 5,188,953 A | 2/1993 | Johnson et al. |
| 5,191,008 A | 3/1993 | Frost et al. |
| 5,196,142 A | 3/1993 | Mollet et al. |
| 5,206,303 A | 4/1993 | Tse et al. |
| 5,207,939 A | 5/1993 | Farng et al. |
| 5,274,060 A | 12/1993 | Schadeli |
| 5,278,055 A | 1/1994 | Cyrus, Jr. et al. |
| 5,304,589 A | 4/1994 | Davidson et al. |
| 5,320,889 A | 6/1994 | Bettle, III |
| 5,449,715 A | 9/1995 | Plochocka et al. |
| 5,498,809 A | 3/1996 | Emert et al. |
| RE35,247 E | 5/1996 | Cyrus, Jr. et al. |
| 5,516,856 A | 5/1996 | Sanchez |
| 5,541,091 A | 7/1996 | Wheeler et al. |
| 5,565,300 A | 10/1996 | Uenishi et al. |
| 5,574,118 A | 11/1996 | Olivier |
| 5,652,201 A | 7/1997 | Papay et al. |
| 5,739,341 A | 4/1998 | Dubs et al. |
| 5,834,544 A | 11/1998 | Lin et al. |
| 5,837,798 A | 11/1998 | Hutchings et al. |
| 5,869,592 A | 2/1999 | Gagne et al. |
| 5,911,937 A | 6/1999 | Hekal |
| 5,994,498 A | 11/1999 | Tripathy et al. |
| 6,018,018 A | 1/2000 | Samuelson et al. |
| 6,046,263 A | 4/2000 | Rasberger et al. |
| 6,096,695 A | 8/2000 | Lam et al. |
| 6,096,859 A | 8/2000 | Akkara et al. |
| 6,150,491 A | 11/2000 | Akkara |
| 6,232,314 B1 | 5/2001 | Jarrott et al. |
| 6,342,549 B1 | 1/2002 | Hirose et al. |
| 6,444,450 B2 | 9/2002 | Akkara et al. |
| 6,646,035 B2 | 11/2003 | Koch et al. |
| 6,723,815 B2 | 4/2004 | Callaghan et al. |
| 6,743,525 B2 | 6/2004 | Berntsen et al. |
| 6,770,785 B1 | 8/2004 | Desai et al. |
| 6,794,480 B2 | 9/2004 | Goto et al. |
| 6,800,228 B1 | 10/2004 | Semen |
| 6,828,364 B2 | 12/2004 | Gugumus |
| 7,132,496 B2 | 11/2006 | Kerres et al. |
| 7,169,844 B2 | 1/2007 | Inokami |
| 7,205,350 B2 | 4/2007 | Thibaut |
| 7,223,432 B2 | 5/2007 | Cholli et al. |
| 7,262,319 B2 | 8/2007 | Rehm et al. |
| 7,705,176 B2 | 4/2010 | Cholli et al. |
| 7,956,153 B2 | 6/2011 | Cholli et al. |
| 8,008,423 B2 | 8/2011 | Kumar et al. |
| 8,039,673 B2 | 10/2011 | Cholli et al. |
| 8,080,689 B2 | 12/2011 | Kumar |
| 8,242,230 B2 | 8/2012 | Cholli et al. |
| 8,252,884 B2 | 8/2012 | Kumar et al. |
| 2001/0041203 A1 | 11/2001 | Uno et al. |
| 2002/0007020 A1 | 1/2002 | Higashimura et al. |
| 2002/0128493 A1 | 9/2002 | Romanczyk, Jr. et al. |
| 2002/0143025 A1 | 10/2002 | Pratt et al. |
| 2002/0183470 A1 | 12/2002 | Tripathy et al. |
| 2003/0030033 A1 | 2/2003 | Duyck et al. |
| 2003/0078346 A1 | 4/2003 | Nakamura et al. |
| 2003/0091837 A1 | 5/2003 | Aoki |
| 2003/0176620 A1 | 9/2003 | Romanczyk, Jr. et al. |
| 2003/0191242 A1 | 10/2003 | Zedda et al. |
| 2003/0229196 A1 | 12/2003 | Braat et al. |
| 2003/0230743 A1 | 12/2003 | Cholli et al. |
| 2004/0015021 A1 | 1/2004 | Adams et al. |
| 2004/0164279 A1 | 8/2004 | Stevenson et al. |
| 2004/0180994 A1 | 9/2004 | Pearson et al. |
| 2004/0186167 A1 | 9/2004 | Ping |
| 2004/0186214 A1 | 9/2004 | Li et al. |
| 2004/0198875 A1 | 10/2004 | Kaprinidis et al. |
| 2004/0214935 A1 | 10/2004 | Cholli et al. |
| 2005/0170978 A1 | 8/2005 | Migdal et al. |
| 2005/0209379 A1 | 9/2005 | Botkin et al. |
| 2005/0238789 A1 | 10/2005 | Cholli et al. |
| 2005/0242328 A1 | 11/2005 | Baranski |
| 2006/0029706 A1 | 2/2006 | Cholli et al. |
| 2006/0040833 A1 | 2/2006 | Al-Akhdar et al. |
| 2006/0041087 A1 | 2/2006 | Cholli |
| 2006/0041094 A1 | 2/2006 | Cholli |
| 2006/0128929 A1 | 6/2006 | Yang et al. |
| 2006/0128930 A1 | 6/2006 | Dhawan et al. |
| 2006/0128931 A1 | 6/2006 | Kumar et al. |
| 2006/0128939 A1 | 6/2006 | Kumar et al. |
| 2006/0154818 A1 | 7/2006 | Destro et al. |
| 2006/0189820 A1 | 8/2006 | Rehm et al. |
| 2006/0189824 A1 | 8/2006 | Kumar et al. |
| 2006/0208227 A1 | 9/2006 | Shiraki |
| 2006/0233741 A1 | 10/2006 | Kumar et al. |
| 2007/0010632 A1 | 1/2007 | Kaplan et al. |
| 2007/0106059 A1 | 5/2007 | Cholli et al. |
| 2007/0135539 A1 | 6/2007 | Cholli et al. |
| 2007/0149660 A1 | 6/2007 | Kumar et al. |
| 2007/0154430 A1 | 7/2007 | Cholli et al. |
| 2007/0154608 A1 | 7/2007 | Cholli et al. |
| 2007/0154720 A1 | 7/2007 | Cholli et al. |
| 2007/0161522 A1 | 7/2007 | Cholli et al. |
| 2008/0249335 A1 | 10/2008 | Cholli et al. |
| 2008/0293856 A1 | 11/2008 | Kumar et al. |
| 2008/0311065 A1 | 12/2008 | Cholli |
| 2009/0184294 A1 | 7/2009 | Cholli et al. |
| 2011/0040125 A1 | 2/2011 | Kumar et al. |
| 2011/0282098 A1 | 11/2011 | Cholli et al. |
| 2012/0004150 A1 | 1/2012 | Cholli et al. |
| 2012/0071596 A1 | 3/2012 | Kumar et al. |
| 2012/0123145 A1 | 5/2012 | Cholli et al. |
| 2013/0041171 A1 | 2/2013 | Cholli et al. |
| 2013/0072586 A1 | 3/2013 | Kumar et al. |
| 2013/0130955 A1 | 5/2013 | Cholli et al. |

FOREIGN PATENT DOCUMENTS

| | | |
|---|---|---|
| DE | 198 43 875 A1 | 3/2000 |
| EP | 0 181 023 A1 | 5/1986 |
| EP | 0 289 077 A2 | 11/1988 |
| EP | 0 358 157 A1 | 3/1990 |
| EP | 0 404 039 A1 | 12/1990 |
| EP | 0 618 203 A1 | 10/1994 |
| EP | 0 688 805 A1 | 12/1995 |
| EP | 1 067 144 A1 | 1/2001 |
| EP | 1 468 968 A1 | 10/2004 |
| FR | 2 183 973 | 12/1973 |
| GB | 1 042 639 | 8/1964 |
| GB | 1 283 103 | 7/1972 |
| GB | 1 320 169 | 6/1973 |
| GB | 1 372 042 | 10/1974 |
| GB | 1 389 442 | 4/1975 |
| GB | 1 469 245 | 4/1977 |
| GB | 1 482 649 | 8/1977 |
| JP | 69002715 B | 1/1966 |
| JP | 43016392 B4 | 7/1968 |
| JP | 44024274 | 10/1969 |
| JP | 44028850 | 11/1969 |
| JP | 45 2980 | 1/1970 |
| JP | 49 29339 | 3/1974 |
| JP | 57085366 A | 5/1982 |
| JP | 59025814 | 2/1984 |

(56) References Cited

FOREIGN PATENT DOCUMENTS

| | | |
|---|---|---|
| JP | 59197447 | 11/1984 |
| JP | 60-199832 | 10/1985 |
| JP | 05 199858 | 8/1993 |
| JP | 06135876 A | 5/1994 |
| JP | 06 247959 | 9/1994 |
| JP | 08027226 A | 1/1996 |
| JP | 09262069 | 10/1997 |
| JP | 09 328519 | 12/1997 |
| JP | 09 328521 | 12/1997 |
| JP | 9322784 A | 12/1997 |
| JP | 11-80063 | 3/1999 |
| JP | 11-158103 | 6/1999 |
| JP | 2003138258 | 5/2003 |
| NL | 7 905 000 | 3/1980 |
| WO | WO 92/20734 | 11/1992 |
| WO | WO 00/39064 A1 | 7/2000 |
| WO | WO 01/18125 A1 | 3/2001 |
| WO | WO 01/48057 A1 | 7/2001 |
| WO | WO 02/079130 A1 | 10/2002 |
| WO | WO 03/087260 A1 | 10/2003 |
| WO | WO 03/102004 A1 | 12/2003 |
| WO | WO 2004/024070 A2 | 3/2004 |
| WO | WO 2004/050795 A2 | 6/2004 |
| WO | WO 2005/025513 A2 | 3/2005 |
| WO | WO 2005/025646 A2 | 3/2005 |
| WO | WO 2005/060500 A2 | 7/2005 |
| WO | WO 2005/070974 A2 | 8/2005 |
| WO | WO 2005/071005 A1 | 8/2005 |
| WO | WO 2006/018403 A1 | 2/2006 |
| WO | WO 2006/060801 A2 | 6/2006 |
| WO | WO 2006/104957 A2 | 10/2006 |
| WO | WO 2008/005358 | 1/2008 |

OTHER PUBLICATIONS

Ayyagari, M.S., et al., "Controlled Free-Radical Polymerization of Phenol Derivatives by Enzyme-Catalyzed Reactions in Organic Solvents," *Macromolecules*, 28(15):5192-5197 (1995).

Badamali, S.K., et al., "Influence of Aluminium Sources on the Synthesis and Catalytic Activity of Mesoporous AlMCM-41 Molecular Sieves," *Catal. Today* 63:291-295 (2000).

Belyaev, A., et al., "Structure-Activity Relationship of Diaryl Phosphonate Esters as Potent Irreversible Dipeptidyl Peptidase IV Inhibitors," *J. Med. Chem.*, 42:1041-1052 (1999).

Blokhin, Y.I, et al., "Phosphorylation of Dihydric Phenols with Amides of Phosphorous Acid," *Russian Chem. Bulletin*, 45(9):2250-2251 (1996).

Bruno, F.F., et al., "Enzymatic Template Synthesis of Polyphenol," Materials Research Society Symposium Proceedings vol. 600, Electroactive Polymers (EAP):255-259 (1999).

Chandra, K.G. and Sharma, M.M., "Alkylation of Phenol with MTBE and Other tert-butylethers:Cation Exchange Resins as Catalysts," *Catal. Lett.* 19(4):309-317 (1993).

Circ-Marjanovic, et al., Chemical Oxidative Polymerization of Aminodiphenylamines, Journal of Physical Chemistry B, 112, 23: 6976-6987 (2008).

Coppinger, G.B., et al., "Photo-Fries Rearrangement of Aromatic Esters. Role of Steric and Electronic Factors" *J. of Phy. Chem.*, 70(11):3479-3489 (1966).

Database Beilstein [online] Beilstein Institut Zur Förderung Der Chemischen Wissenschaften; XP002420027, Beilstein Registry No. 3517906.

Database Beilstein [online] Beilstein Institut Zur Förderung Der Chemischen Wissenschaften; XP002420028, Beilstein Registry No. 5840042.

Database Beilstein [online] Beilstein Institut Zur Förderung Der Chemischen Wissenschaften; XP002420029, Beilstein Registry No. 2311871.

Database Beilstein [online] Beilstein Institut Zur Förderung Der Chemischen Wissenschaften; XP002420030, Beilstein Registry No. 8876646.

Database Beilstein [online] Beilstein Institut Zur Förderung Der Chemischen Wissenschaften; XP002420031, Beilstein Registry No. 2271400.

Database Beilstein [online] Beilstein Institut Zur Förderung Der Chemischen Wissenschaften; XP002420032, Beilstein Registry No. 2212095.

Database Beilstein [online] Beilstein Institut Zur Förderung Der Chemischen Wissenschaften; XP002420033, Beilstein Registry No. 8941955.

Database Beilstein [online] Beilstein Institut Zur Förderung Der Chemischen Wissenschaften; XP002420034, Database Accession No. 2312425.

Database Beilstein [online] Beilstein Institut Zur Förderung Der Chemischen Wissenschaften; XP002420035, Beilstein Registry No. 905950.

Database Beilstein [online] Beilstein Institut Zur Förderung Der Chemischen Wissenschaften; XP002420036, Beilstein Registry No. 2140308.

Database Beilstein [online] Beilstein Institut Zur Förderung Der Chemischen Wissenschaften; XP002420037, Beilstein Registry No. 134886.

Database Beilstein [online] Beilstein Institut Zur Förderung Der Chemischen Wissenschaften; XP002420038, Beilstein Registry No. 1961007.

Database CA [online] Chemical Abstracts Service, Columbus, Ohio, US, XP-002429584, Database Accession No. 81::153647, Organic Phosphate Stabilizers for Polyamides and Polyurethanes, abstract, Minagawa, M. (1974).

Database Caplus [online] Chemical Abstracts Service, Columbus, Ohio, US, XP-002387095, Database Accession No. 1981:572206, Effectiveness of Inhibitors in the Oxidation of Jet Fuel with an Initiator, abstract, Kovalev, et al.

Devassy, B.M., et al., "Zirconia Supported Phosphotungstic Acid as an Efficient Catalyst for Resorcinol *tert*-Butylation and *n*-Heptane Hydroisomerization," *J. Mol. Catalysis A: Chemical* 221:113-119 (2004).

Ding, et al., "Chemical Trapping Experiments Support a Cation-Radical Mechanism for the Oxidative Polymerization of Aniline," Journal of Polymer Science, Part A: Polymer Chemistry, vol. 37: 2569-2579 (1999).

Dordick, J.S., "Enzymatic Catalysis in Monophasic Organic Dolvents," *Enzyme Microb. Technol.*, 11(4):194-211 (1989).

Dordick, J.S., et al., "Polymerization of Phenols Catalyzed by Peroxidase in Nonaqueous Media," *Biotechnology and Bioengineering*, XXX:31-36 (1987).

English Abstract of Kovalev, G. I., et al., "Study of the Effectiveness of Inhibitors in Oxidation of Jet Fuel in a Closed Volume," *Deposited Doc.*, VINITI: 443-82 (1981).

English Abstract of Kovalev, G.I., et al., "Effectiveness of Inhibitors in the Oxidation of Jet Fuel With an Initiator," *J. Neftekhimiya* (*Petroleum Chemistry*), 21(2): 287-298 (1981).

Faber, K., "Biotransformations in Organic Chemistry," A Textbook, Fourth Completely Revised and Extended Edition, Springer-Verlag pp. 347-349 (1953).

FS&T 821 "Antioxidant," [online], [retrieved on Oct. 29, 2002]. Retrieved from the Internet <URL: http://class.fst.ohio-state.edu/fst821/>.

FS&T 821 "Food Lipids," [online], Oct. 2001 [retrieved on Oct. 29, 2002]. Retrieved from the Internet <URL: http://class.fst.ohio-state.edu/fst821/>.

FST 821 "Course Schedule," [online], [retrieved on Oct. 29, 2002]. Retrieved from the Internet <URL: http://class.fst.ohio-state.edu/fst821/>.

Hatayama, K., et al., "Anti-ulcer Effect of Isoprenyl Flavonoids. III.[1)] Synthesis and Anti-ulcer Activity of Metabolites of 2'-Carboxymethoxly-4,4'-bis(3-methyl-2-butenyloxy)chalcone[2)]," *Chemical & Pharmaceutical Bulletin*, 33(4), 1327-1333(Apr. 1985).

Heidekum, A., et al., "Nafion/Silica Composite Material Reveals High Catalytic Potential in Acylation Reactions," *J. Catal.* 188:230-232 (1999).

Hidalgo, M.E., et al., "Antioxidant Activity of Depsides and Depsidones," Phytochemistry, 37(6):1585-1587 (1994).

(56) References Cited

OTHER PUBLICATIONS

Hofer, K., et al.,"[[(Anilinooxalyl)amino]phenyl] Phosphite Stabilizers for Polypropylene," Chemical Abstracts Service, ZCAPLUS, document No. 77:62780 (1972).

Ikeda, R., et al., "Novel Synthetic Pathway to a Poly(phenylene oxide). Laccase-Catalyzed Oxidative Polymerization of Syringic Acid," *Macromolecules*, 29:3053-3054 (1996).

International Search Report for related foreign application PCT/US2007/015177, mailed on Jun. 13, 2008.

International Search Report for related foreign application PCT/US2005/044021, mailed on May 22, 2006.

International Search Report for related foreign application PCT/US2005/044022, mailed on May 2, 2006.

International Search Report for related foreign application PCT/US2005/044023, mailed on Nov. 3, 2006.

International Search Report for related foreign application PCT/US2005/044019, mailed on Apr. 28, 2006.

International Search Report for related foreign application PCT/US2005/025646, mailed on Mar. 13, 2006.

International Search Report for related foreign application PCT/US2005/025513, mailed on Mar. 13, 2006.

International Search Report for related foreign application PCT/US2006/006355, mailed on Jul. 31, 2006.

International Search Report for related foreign application PCT/US2006/010985, mailed on Dec. 19, 2006.

International Search Report for related foreign application PCT/US2006/042240, mailed on May 3, 2007.

International Search Report for related foreign application PCT/US2006/042235, mailed on Apr. 27, 2007.

International Search Report for related foreign application PCT/US2006/045929, mailed on Apr. 20, 2007.

International Search Report in related foreign application PCT/US2006/042251, mailed Feb. 22, 2007.

Ismail, M.N. and Wazzan, A.A., "Evaluation of New Thermal Stabilizers and Antifatigue Agents for Rubber Vulcanizates," *Polymer-Plastics Tech. and Eng.*, 45:751-758 (2006).

Jayaprakasha, G.K., et al., "Antioxidant Activity of Grape Seed (*Vitis vinifera*) Extracts on Peroxidation Models In Vitro," *Food Chemistry*, 73:285-290 (2001).

Jialanella, G.and Pilrma, I., "Synthesis of Poly(vinyl alcohol-co-vinyl gallate) by the Chemical Modification of Poly(vinyl alcohol)," *Polymer Bulletin* 18:385-389 (1987).

Joossens, J., et al., "Diphenyl Phosphonate Inhibitors for the Urokinase-Type Plasminogen Activator: Optimization of the P4 Position," *J. Med. Chem.*, 49:5785-5793 (2006).

Kamitori, Y., et al., "Silica Gel as an Effective Catalyst for the Alkylation of Phenols and Some Heterocylic Aromatic Compounds," *J. Org. Chem.* 49: 4161-4165 (1984).

Kazandjian, R.Z., et al., "Enzymatic Analyses in Organic Solvents," *Biotechnology and* Bioengineering, XXVIII:417-421 (1986).

Khan, K.M., et al., "An Expedient Esterification of Aromatic Carboxylic Acids Using Sodium Bromate and Sodium Hydrogen Sulfite," *Tetrahedron* 59(29):5549-5554 (2003).

Kim, T. H., et al., "Melt Free-Radical Grafting of Hindered Phenol Antioxidant onto Polyethylene," *J. Applied Polymer Science*, 77:2968-2973 (2000).

Klibanov, A.M., et al., "Enzymatic Removal of Toxic Phenols and Anilines from Waste Waters," *J. of Applied Biochemistry*, 2(5):414-421 (1980).

Koshchii, V.A., et al. "Alkylation of Phenol by Alcohols in the Presence of Alumium Phenolate," *Org. Chem.* 24(7):1358-1361 (1988).

Lalancette, J.M., et al.,, "Metals Intercalated in Graphite. II. The Friedel-Crafts Reactions with $ALCL_3$-Graphite," *Can. J. Chem.* 52:589-591 (1974).

Li, et al., "Novel Multifunctional Polymers," Chemical Reviews, vol. 102, No. 9, pp. 5925-2943 (2002).

Maki, M., et al., "Weather-Resistant Colored Polypropylene," Chemical Abstracts Service, ZCAPLUS, document No. 89:111364 (1978).

March, J., Advanced Organic Chemistry, McGraw Hill Book Company, New York, pp. 251-259 (1977).

Masada, H. and Oishi, Y., "A New Synthesis of aryl *t*-butyl Ethers," *Chem. Letters*, 57-58 (1978).

Masada, H. et al., "A New Heterogeneous Williamson Synthesis of Ethers Using *t*-alkyl Substrates," The *Chemical Society of Japan* 3:275-282 (1996).

Masada, H., et al., "A New Method for the Williamson Ether Synthesis Using *t*-alkyl Halides in Nonpolar Solvents," *The Chemical Society of Japan*, 2:164-166 (1995).

Mehdipour-Ataei, S., et al., "Novel Diols Containing Ester and Amide Groups and Resulting Poly(ester amide ester)s," *J. Applied Polymer Sci.*, 93:2699-2703 (2004), XP002420014.

Mejias, L., et al.,, "New Polymers From Natural Phenols Using Horseradish or Soybean Peroxidase," *Macromol. Biosci.*, 2:24-32 (2002).

Notification Concerning Transmittal of International Preliminary Report on Patentability for related foreign application PCT/US2007/015177, mailed on Jan. 15, 2009.

Ol'dekop, Yu. A., et al. "Simple Synthesis of the tert-butyl Ether of Phenol" Inst. Fiz-Org. Khim., Minsk, USSR. *Zhurnal Obshchei Khimii*, 50(2):475-6 (1980).

Overgaag, M., et al., "Rearrangement of Alkyl Phenyl Ethers Over Dealuminated HY Zeolites Under Liquid-Phase Conditions," *Applied Catalysis A: General, Elsevier Sci.*, 175(1-2):139-146 (1998).

Pätoprstý, V., et al., "$^{13}$C NMR Study of 3,9-Di(alkylphenoxy)-2,4,8,10-tetraoxa-3,9-diphosphaspiro[5.5]undecanes," *Magnetic Resonance in Chem*, 23(2):122-126 (1985).

Pirozhenko, V.V., et al., "NMR Study of Topomerization of *N*-Aroyl-*p*-Benzoquinonemonoimines," *Russian J. of Organic Chem.*, 31(11):1514-1519 (1995).

Quaschning, V., et al., "Properties of Modified Zirconia Used as Friedel-Crafts-Acylation Catalysts," *J. Catal.* 177:164-174 (1998).

Ryu, K., et al., "Peroxidase-Catalyzed Polymerization of Phenols," Biocatalysis in Agricultural Biotechnology, Chapter10:141-157 (1988).

Sakthivel, A., et al., "Vapour Phase Tertiary Butylation of Phenol Over Sulfated Zirconia Catalyst," *Catal. Lett.*, 72(3-4):225-228 (2001).

Sartori G., et al., "Highly Selective Mono-*tert*-butylation of Aromatic Compounds," *Chem. Ind.*, (London), (22):762-763 (1985).

Scharpe, S.L., et al., "Serine Peptidase Modulators, Their Preparation, and Their Therapeutic Use," Chemical Abstracts Service, ZCAPLUS, document No. 131:223514 (1999).

Singh, A. and Kaplan, D. L., "Biocatalytic Route to Ascorbic Acid-Modified Polymers for Free-Radical Scavenging," *Adv. Matter.*, 15(15):1291-1294 (2003).

Spano, R., et al., "Substituted Anilides of 3-Monoethyl Ester of 4 Hydroxyisophthalic Acid," *J. of Med. Chem.*, 15(5):552-553 (1972).

Thompson, C.R., et al., "Stability of Carotene in Alfalfa Meal: Effect of Antioxidants," *Industrial and Engineering Chemistry*, Western Regional Research Laboratory, Albany, Calif., 42(5); 922-925 (May 1950).

Tsvetkov, O.N., et al., "Alkylation of Phenols with Higher Olefins. Part I," *Int. Chem. Eng.* 7(1):104-121 (1967).

Written Opinion for related foreign application PCT/US2007/015177, mailed on Jan. 15, 2009.

XP-002419239, "Discover Our World of Effects for Polyolefins," *Ciba Speciality Chemicals*, (2003).

Al-Malaika, S and Suharty, N., "Reactive Processing of Polymers: Mechanisms of Grafting Reactions of Functional Antioxidants on Polyolefins in the Presence of a Coagent," Polymer Degradation and Stability 49: 77-89 (1995).

Written Opinion for related foreign application PCT/US2005/025646, mailed on Nov. 14, 2006.

Notification Concerning Transmittal of International Preliminary Report on Patentability for related foreign application PCT/US2005/025646, mailed on Nov. 14, 2006.

(56) References Cited

OTHER PUBLICATIONS

International Preliminary Report on Patentability and Written Opinion for related foreign application PCT/US2005/025513, mailed on Jan. 23, 2007.
RN 85650-63-1, 1984.
Notification Concerning Transmittal of International Preliminary Report on Patentability for related foreign application PCT/US2005/001946, mailed on Aug. 3, 2006.
Notification Concerning Transmittal of International Preliminary Report on Patentability for application PCT/US2006/042251, mailed on May 8, 2008.

Irgafos® 126, BASF publication, pp. 1-3, Jul. 2010.

USPTO Search Report for U.S. Appl. No. 13/572,884, filed Mar. 20, 2013.

* cited by examiner

NITROGEN AND HINDERED PHENOL CONTAINING DUAL FUNCTIONAL MACROMOLECULAR ANTIOXIDANTS: SYNTHESIS, PERFORMANCES AND APPLICATIONS

RELATED APPLICATION

This application is a continuation of U.S. application Ser. No. 12/854,347, filed Aug. 11, 2010 now U.S. Pat. No. 8,080,689, which is a divisional of U.S. application Ser. No. 11/360,020, filed Feb. 22, 2006 now U.S. Pat. No. 7,799,948, which claims the benefit of U.S. Provisional Application No. 60/655,169, filed on Feb. 22, 2005. The entire teachings of the above applications are incorporated herein by reference.

BACKGROUND OF THE INVENTION

Antioxidants are employed to prevent oxidation in a wide range of materials, for example, plastics, elastomers, lubricants, petroleum based products (lubricants, gasoline, aviation fuels, and engine oils), cooking oil, cosmetics, processed food products, and the like. While many antioxidants exist, there is a continuing need for new antioxidants that have improved properties.

SUMMARY OF THE INVENTION

The present invention relates to compounds containing dual functionalities of aromatic amines and hindered phenols that can be useful as stabilizers for organic materials, lubricants and petroleum based products, plastics and elastomers, cosmetics, foods and cooking oils, and other materials. In particular, the present invention pertains to highly effective antioxidant macromolecules described herein. This invention also reports an improved, highly efficient and economical process for the synthesis of amine (nitrogen) and sterically hindered phenol containing dual functional macromolecules. The design of macromolecules in this invention can incorporate at least two antioxidant moieties having different reactivities. The present invention also discloses their superior antioxidant performance compared to presently used commercial antioxidants. This is demonstrated especially in both synthetic and petroleum base stocks (Group I, II and III). In general one unique feature and design of the antioxidants described herein is their improved solubility in many commercially available oils and lubricants compared with currently available antioxidants.

In one embodiment the present invention is a compound represented by structural formula (I):

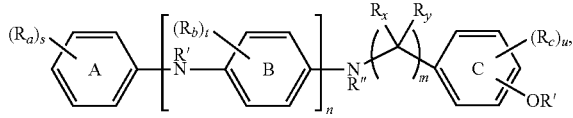

Each $R_a$ is independently an optionally substituted alkyl. Each $R_b$ is independently an optionally substituted alkyl. Each $R_c$ is independently an optionally substituted alkyl or an optionally substituted alkoxycarbonyl. $R_x$ is —H or an optionally substituted alkyl. $R_y$ is —H or an optionally substituted alkyl. Each R' is independently —H or an optionally substituted alkyl. R" is —H, an optionally substituted alkyl, an optionally substituted aryl or an optionally substituted aralkyl. n is an integer from 1 to 10. m is an integer from 1 to 10. s is an integer from 0 to 5. t is an integer from 0 to 4. u is an integer from 1 to 4. With the proviso that when n is 1, then either ring C is not:

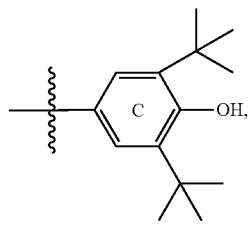

s is not 0, or R" is not —H.

In another embodiment, the present invention is a method of producing a compound represented structural formula (I). The method comprises combining a phenol derivative, an amine and an aldehyde in the presence of a solvent, wherein the phenol derivative comprises at least one unsubstituted ring-carbon atom. Followed by refluxing the combination to produce the compound, and finally isolating the compound.

In yet another embodiment, the present invention is a method of producing a compound represented structural formula (I). The method comprises combining a amino-phenol derivative with an amine in the presence of a solvent. Followed by refluxing the combination to produce the compound, and finally isolating the compound.

In yet another embodiment, the present invention is a method of producing a compound represented structural formula (I). The method comprises combining a phenolic-carbonyl derivative represented by the following structural formula:

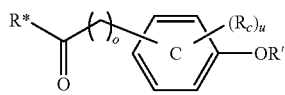

with an amine in the presence of a solvent. Followed by refluxing the combination to produce a schiff's base, reducing the schiff's base with a reducing agent to produce the compound, and finally isolating the compound.

In another embodiment, the present invention is a method of producing a compound represented structural formula (I). The method comprises combining a formaldehyde-sodium bisulfite adduct with an amine to produce a methylsulfonate sodium salt in an aqueous media. Followed by the nucleophilic displacement of the sulfonate group with a sodium or potassium salt of a phenol derivative, in an aqueous media wherein the nucleophilic displacement is catalyzed by base, to produce the compound, and finally isolating the compound.

In another embodiment the present invention is a method of preventing oxidation in an oxidizable material, comprising combining the oxidizable material with a compound of the present invention.

The antioxidants described herein which are prepared by the disclosed processes in general are superior antioxidants (compared to currently available antioxidants) against oxidative, thermal degradation of organic materials. These macromolecular antioxidants generally have comparatively higher antioxidant activities along with improved thermal stability and performance in a wide range of materials including but not limited to plastics, elastomers, lubricants, petroleum based products (lubricants, gasoline, aviation fuels, and engine oils), cooking oil, cosmetics, processed food products.

The processes of the present invention have many advantages which can allow improved synthesis of these macromolecular antioxidants. For example, the disclosed processes can be economically carried out in the melt phase without the presence of catalysts. Moreover, the processes described herein generally reduce or eliminate purification steps for the final product compared to existing syntheses, which can lead to a superior performance/cost ratio for the product and reduced amounts of waste.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
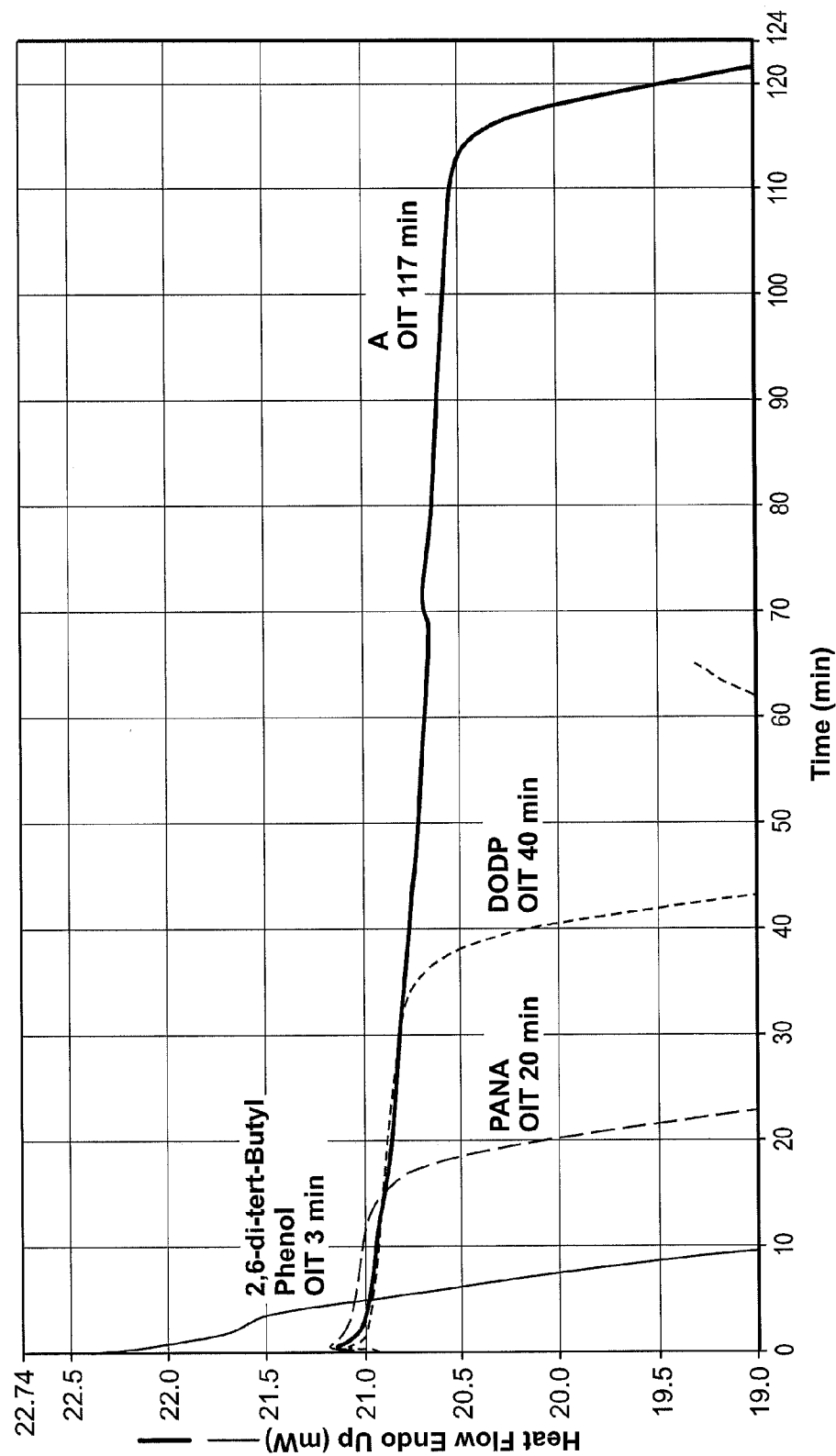
FIG. 1, is a graph of Oxidative Induction Time (OIT) values of Structural Formula A of the invention versus Commercial antioxidants (AO's) in Group II Lubricating Oils.

A description of preferred embodiments of the invention follows.

As used herein, "dual functional" means any molecule with two functional groups which can optionally be the same or in certain embodiment are different, such as amine and hydroxy.

As used herein "adduct" means chemically linked.

Sterically hindered, as used herein means that the substituent group (e.g., bulky alkyl group) on a ring carbon atom adjacent (or para) to a ring carbon atom substituted with a phenolic hydroxy group (or thiol or amine group), is large enough to sterically hinder the phenolic hydroxy group (or thiol or amine groups). This steric hindrance, in certain embodiments results in more labile or weak bonding between the oxygen and the hydrogen (or sulfur or nitrogen and hydrogen) and in turn enhances the stability and antioxidant activity (proton donating activity) of the sterically hindered antioxidant.

Repeat units of the antioxidants of the invention include substituted benzene molecules. Some of these benzene molecules are typically based on phenol or a phenol derivative, such that they have at least one hydroxyl or ether functional group. In certain embodiments, the benzene molecules have a hydroxyl group. The hydroxyl group can be a free hydroxyl group and can be protected or have a cleavable group attached to it (e.g., an ester group). Such cleavable groups can be released under certain conditions (e.g., changes in pH), with a desired shelf life or with a time-controlled release (e.g., measured by the half-life), which allows one to control where and/or when an antioxidant can exert its antioxidant effect. The repeat units can also include analogous thiophenol and aniline derivatives, e.g., where the phenol —OH can be replaced by —SH, —NH—, and the like.

Substituted benzene repeat units of an antioxidant of the invention are also typically substituted with a bulky alkyl group or an n-alkoxycarbonyl group. In certain embodiments, the benzene monomers are substituted with a bulky alkyl group. In certain other embodiments, the bulky alkyl group is located ortho or meta to a hydroxyl group on the benzene ring, typically ortho. A "bulky alkyl group" is defined herein as an alkyl group that is branched alpha- or beta- to the benzene ring. In certain other embodiments, the alkyl group is branched alpha to the benzene ring. In certain other embodiments, the alkyl group is branched twice alpha to the benzene ring, such as in a tert-butyl group. Other examples of bulky alkyl groups include isopropyl, 2-butyl, 3-pentyl, 1,1-dimethylpropyl, 1-ethyl-1-methylpropyl and 1,1-diethylpropyl. In certain other embodiments, the bulky alkyl groups are unsubstituted, but they can be substituted with a functional group that does not interfere with the antioxidant activity of the molecule. Straight chained alkoxylcarbonyl groups include methoxycarbonyl, ethoxycarbonyl, n-propoxycarbonyl, n-butoxycarbonyl and n-pentoxycarbonyl. N-propoxycarbonyl is a preferred group. Similar to the bulky alkyl groups, n-alkoxycarbonyl groups are optionally substituted with a functional group that does not interfere with the antioxidant activity of the molecule.

In one embodiment the present invention is a compound represented by structural formula (I) wherein the variables are as described as follows:

Each $R_a$ is independently an optionally substituted alkyl. In one embodiment, each $R_a$ is independently a C1-C20 alkyl. In another embodiment, each $R_a$ is independently a C1-C10 alkyl. In another embodiment, each $R_a$ is independently selected from the group consisting of:

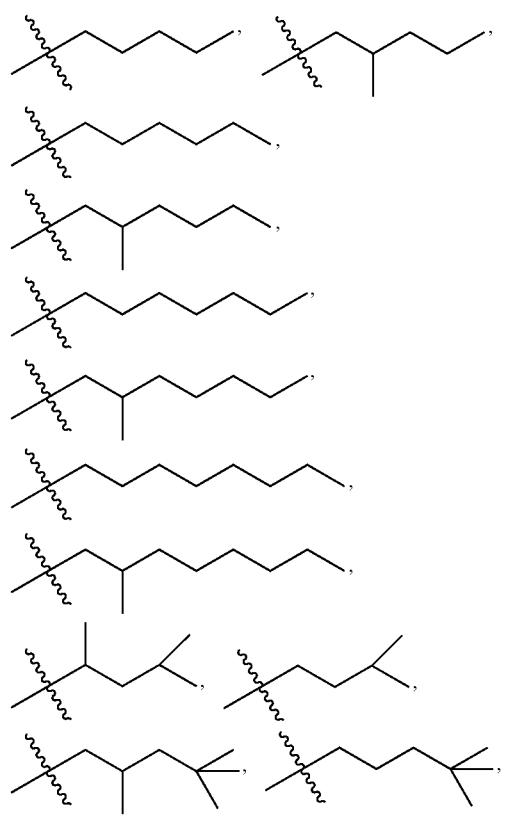

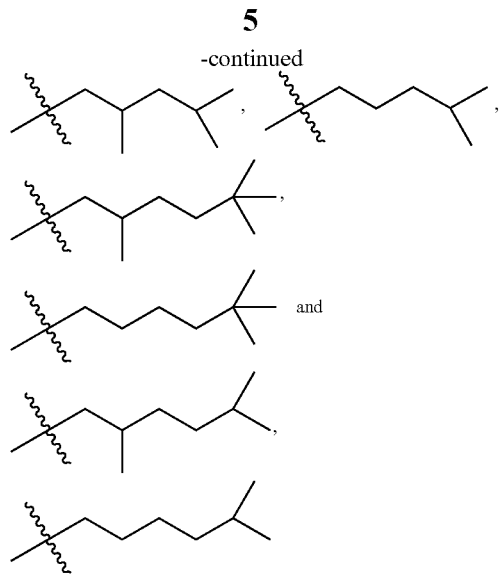

In another embodiment $R_a$ is:

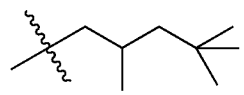 [SMILES: *CC(C)CC(C)(C)C]

Each $R_b$ is independently an optionally substituted alkyl.

Each $R_c$ is independently an optionally substituted alkyl or an optionally substituted alkoxycarbonyl. In one embodiment, each $R_c$ is independently a C1-C10 alkyl.

$R_x$ is —H or an optionally substituted alkyl. $R_y$ is —H or an optionally substituted alkyl. In one embodiment, $R_x$ and $R_y$ are —H.

Each R' is independently —H or an optionally substituted alkyl. In one embodiment, one R' is —H. In another embodiment, both R' are —H.

R" is —H, an optionally substituted alkyl, an optionally substituted aryl or an optionally substituted aralkyl. In one embodiment, R" is —H, a C1-C20 alkyl or an optionally substituted aralkyl. In another embodiment, R" is —H, a C1-C10 alkyl or a substituted benzyl group. In yet another embodiment, R" is —H. In yet another embodiment, R" is:

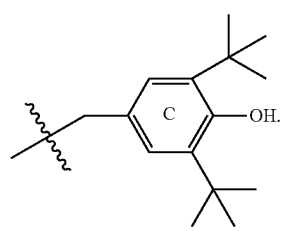

In yet another embodiment R" is selected from the group consisting of:

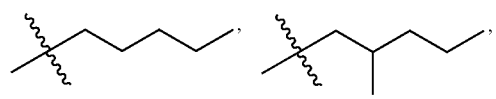

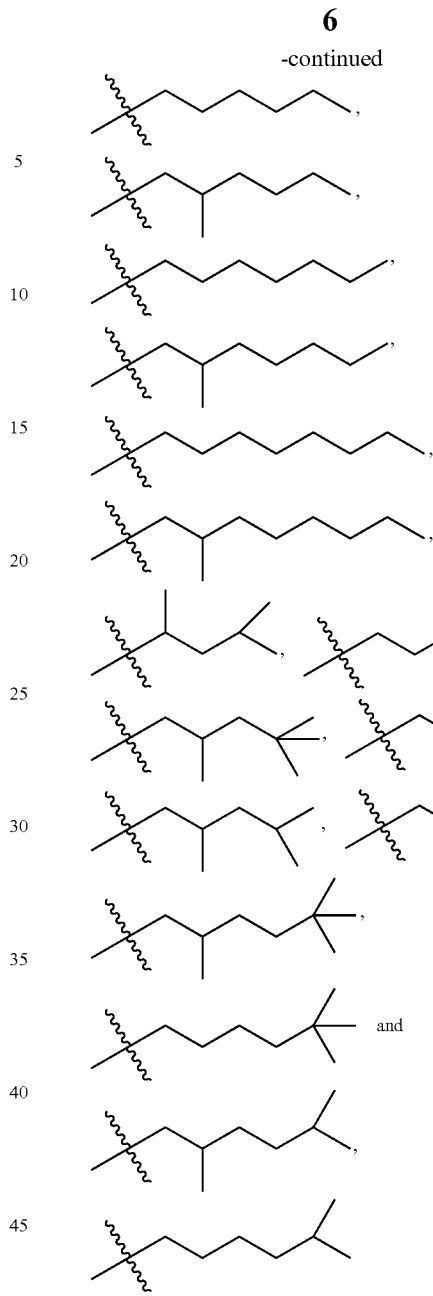

In yet another embodiment R" is:

n is an integer from 1 to 10. In one embodiment, n is an integer from 1 to 6. In another embodiment, n is 1. In yet another embodiment, n is 2. In yet another embodiment, n is 3. In yet another embodiment, n is 4.

m is an integer from 1 to 10. In one embodiment, m is 1 or 2. In another embodiment, m is 1.

s is an integer from 0 to 5. In one embodiment, s is 0 or 1. In another embodiment, s is 0.

t is an integer from 0 to 4. In one embodiment, t is 0.

u is an integer from 1 to 4. In one embodiment, u is 1 or 2.

In certain embodiments for compounds of the present invention, including those represented by structural formula (I), when n is 1, the either ring C is not:

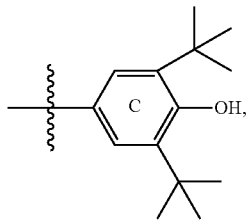

s is not 0, or R" is not —H.

In one embodiment of the present invention for the compounds represented by structural formula (I):

Each $R_a$ is independently a C1-C20 alkyl. Each $R_c$ is independently a C1-C10 alkyl. R" is —H, a C1-C20 alkyl or an optionally substituted aralkyl, and the remainder of the variables are as described above for structural formula (I).

In another embodiment of the present invention for compounds represented by structural formula (I): one R' is —H, t is O, $R_x$ and $R_y$ are —H and the compounds are represented by structural formula (II):

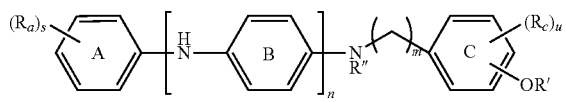

(II)
and the remainder of the variables are as described in the immediately preceding paragraph or for structural formula (I).

In another embodiment of the present invention for the compounds represented by structural formula (II):
m is 1 or 2.
s 0 or 1.
u is 1 or 2, and the remainder of the variables are as described in the immediately preceding paragraph or for structural formula (I).

In another embodiment of the present invention for compounds represented by structural formula (II): both R' are —H and m is 1 and the compounds are represented by structural formula (III):

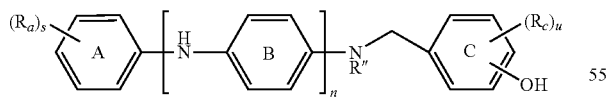

(III)

and the remainder of the variables are as described in the immediately preceding paragraph or for structural formula (I) or (II).

In another embodiment of the present invention for the compounds represented by structural formula (III):
Each $R_a$ is independently a C1-C10 alkyl.
R" is —H, a C1-C10 alkyl or a substituted benzyl group.
n is an integer from 1 to 6, and the remainder of the variables are as described in the immediately preceding paragraph or for structural formula (I) or (II).

In another embodiment of the present invention for compounds represented by structural formula (III): n is 1, s is 0 and R" is —H and the compounds are represented by structural formula (IV):

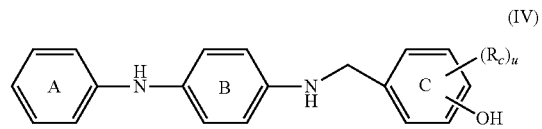

with the proviso that ring C is not:

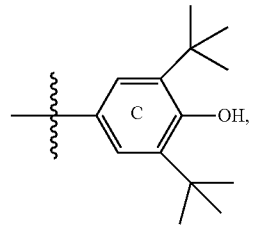

and the remainder of the variables are as described above for structural formula (I), (II) or (III).

In certain embodiments of the present invention the compounds represented by structural formula (III) or (IV) are represented by the following structural formulas:

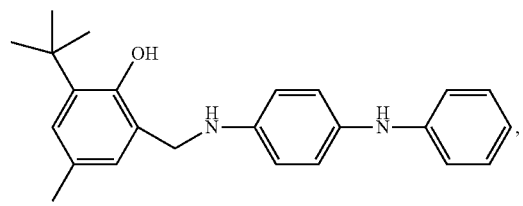

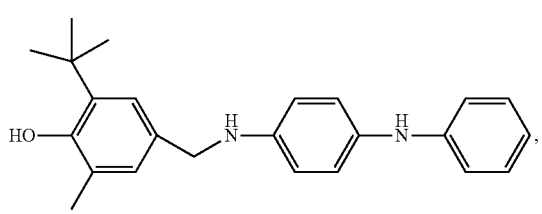

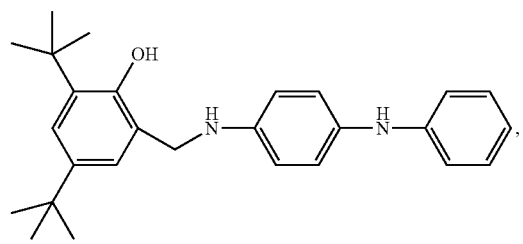

-continued

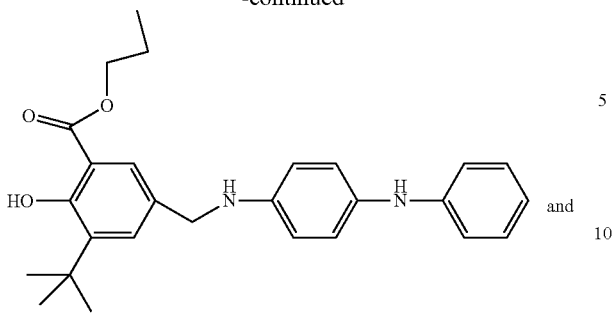

and

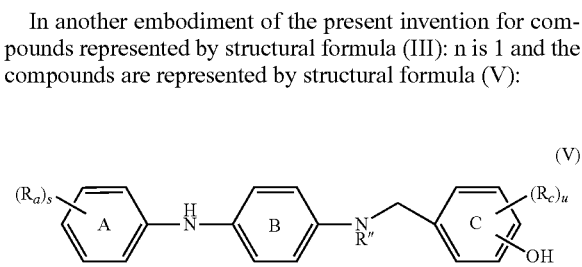

In another embodiment of the present invention for compounds represented by structural formula (III): n is 1 and the compounds are represented by structural formula (V):

(V)

(R$_a$)$_s$—A—N(H)—B—N(R″)—CH$_2$—C—(R$_c$)$_u$, OH and the remainder of the variables are as described above for structural formula (I), (II) or (III).

In another embodiment of the present invention for compounds represented by structural formula (III): s is 0 and the compounds are represented by structural formula (VI):

(VI)

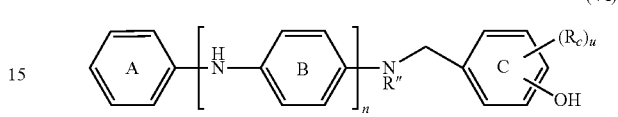

and the remainder of the variables are as described above for structural formula (I), (II) or (III).

In another embodiment of the present invention for compounds represented by structural formula (III): R″ is —H and the compounds are represented by structural formula (VII):

(VII)

and the remainder of the variables are as described above for structural formula (I), (II) or (III).

In certain embodiments of the present invention the compounds represented by structural formula (III), (V), (VI) or (VII) are represented by the following structural formulas:

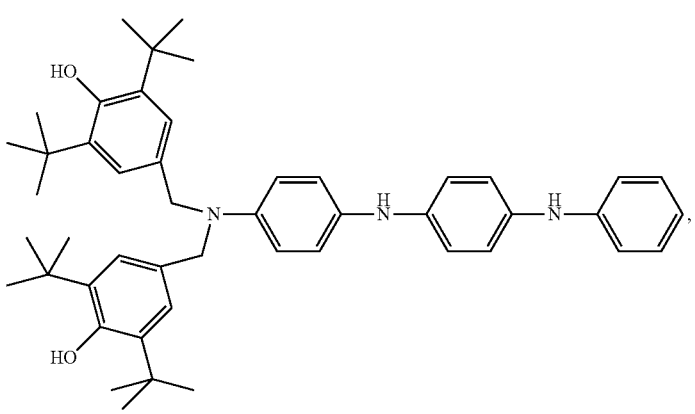

-continued
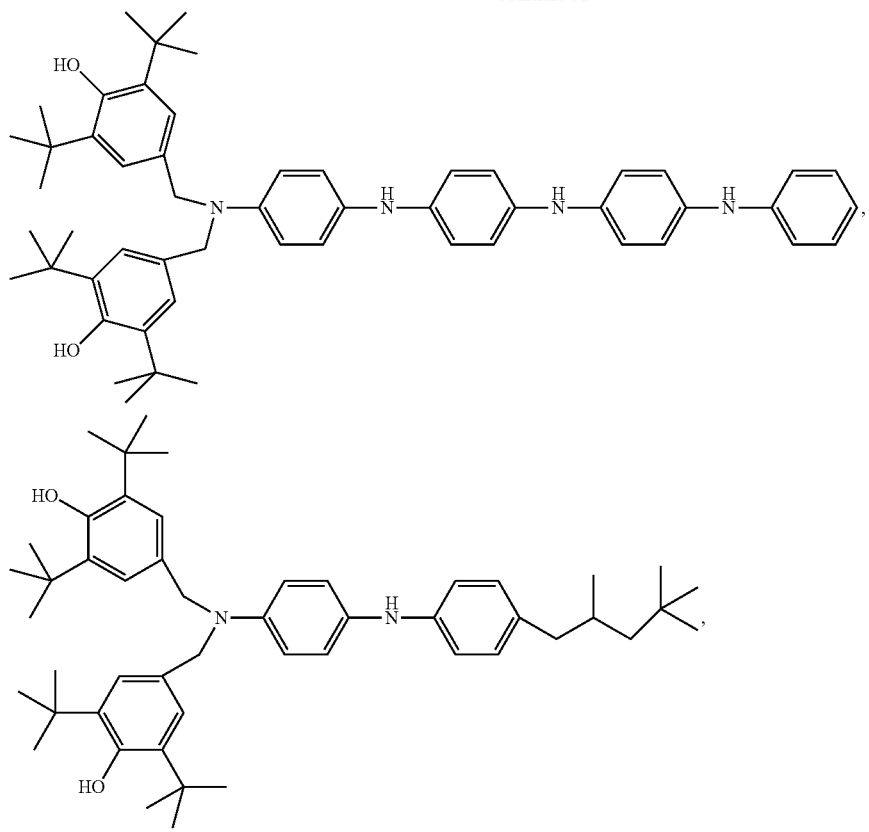
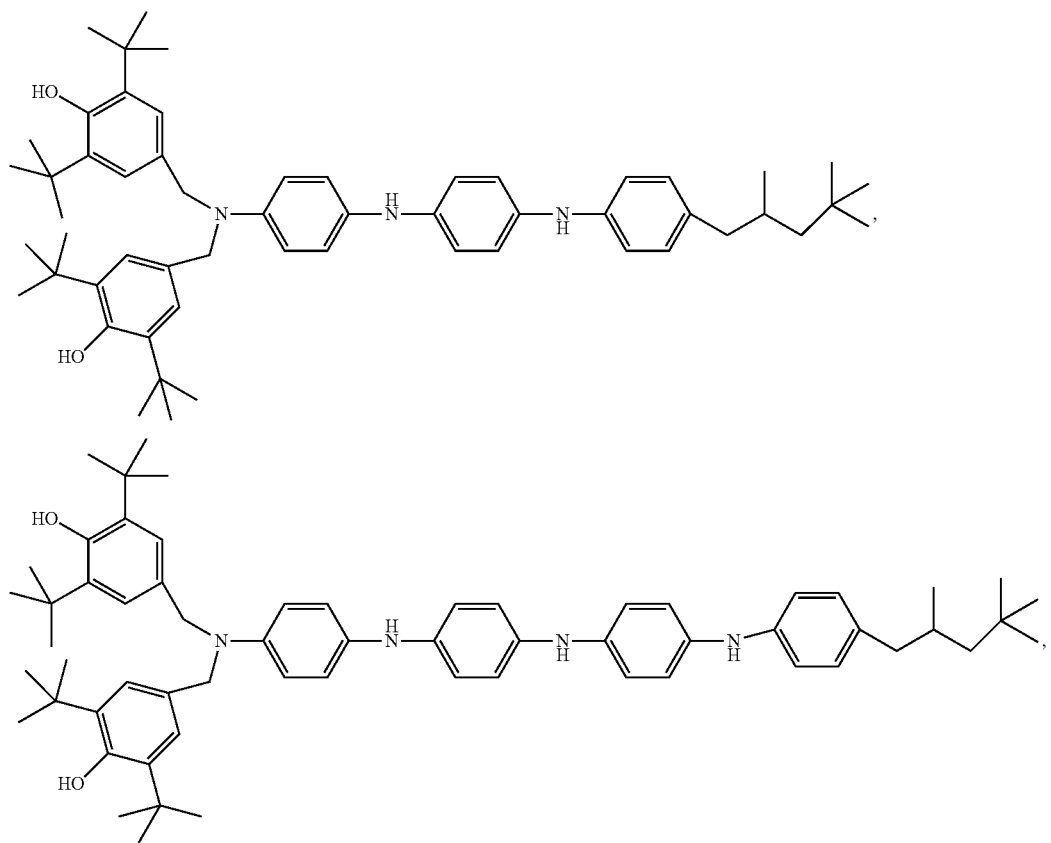

-continued
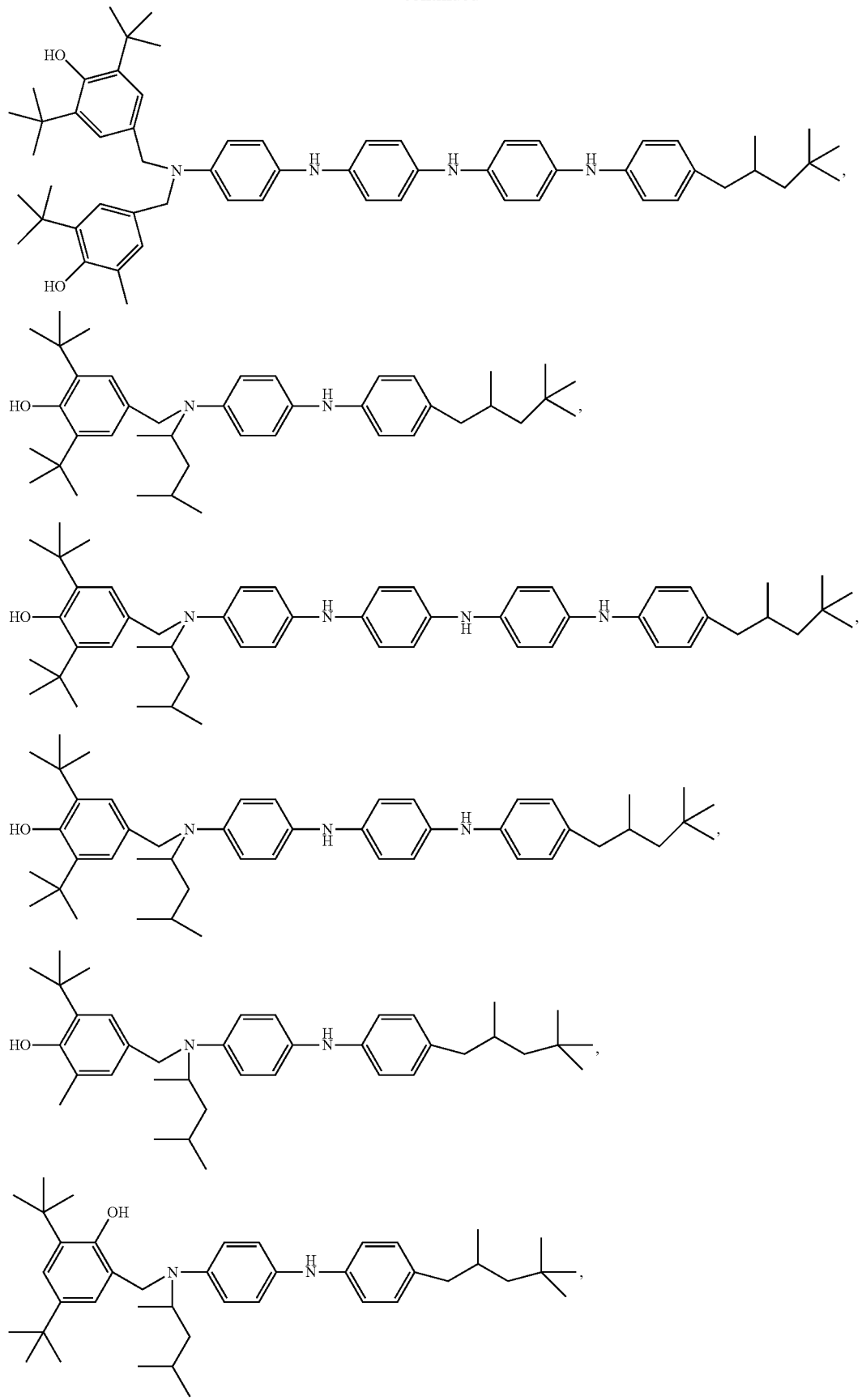

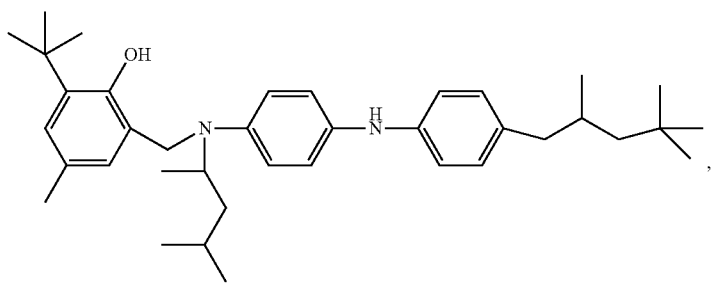,
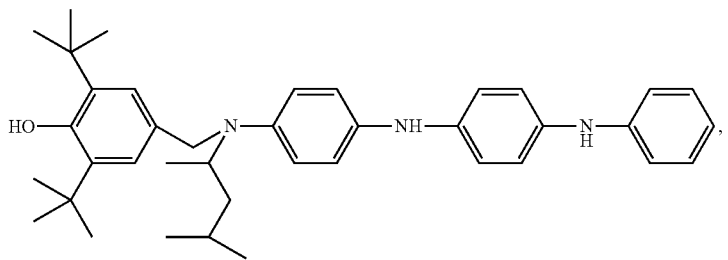,
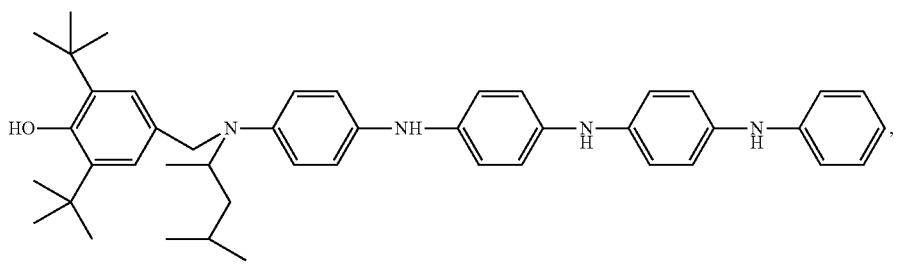,
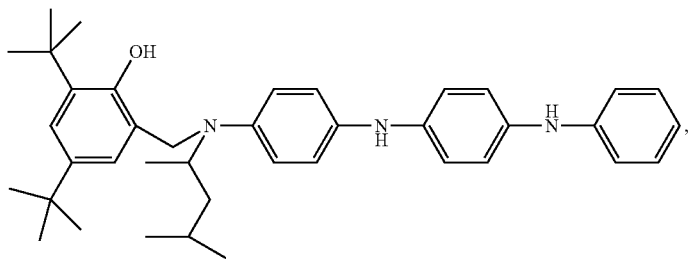,
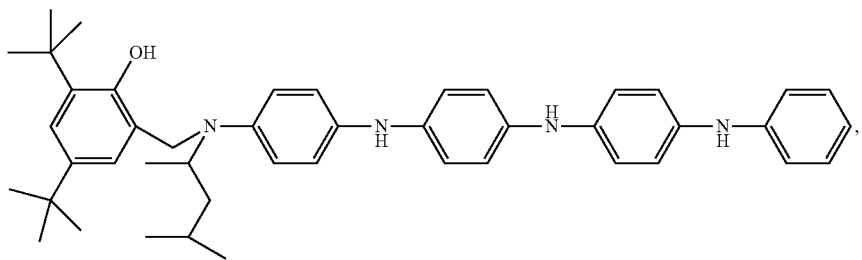,
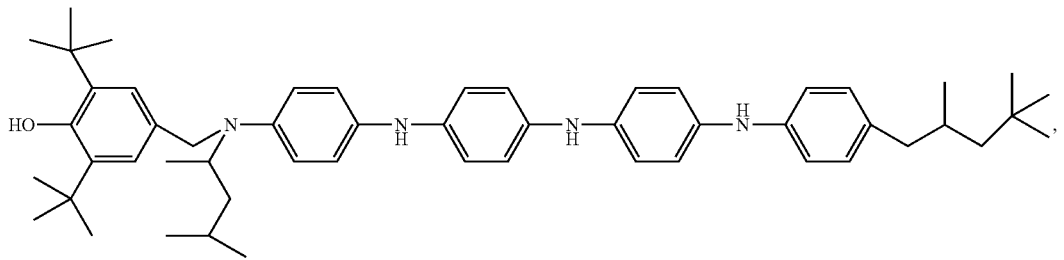,

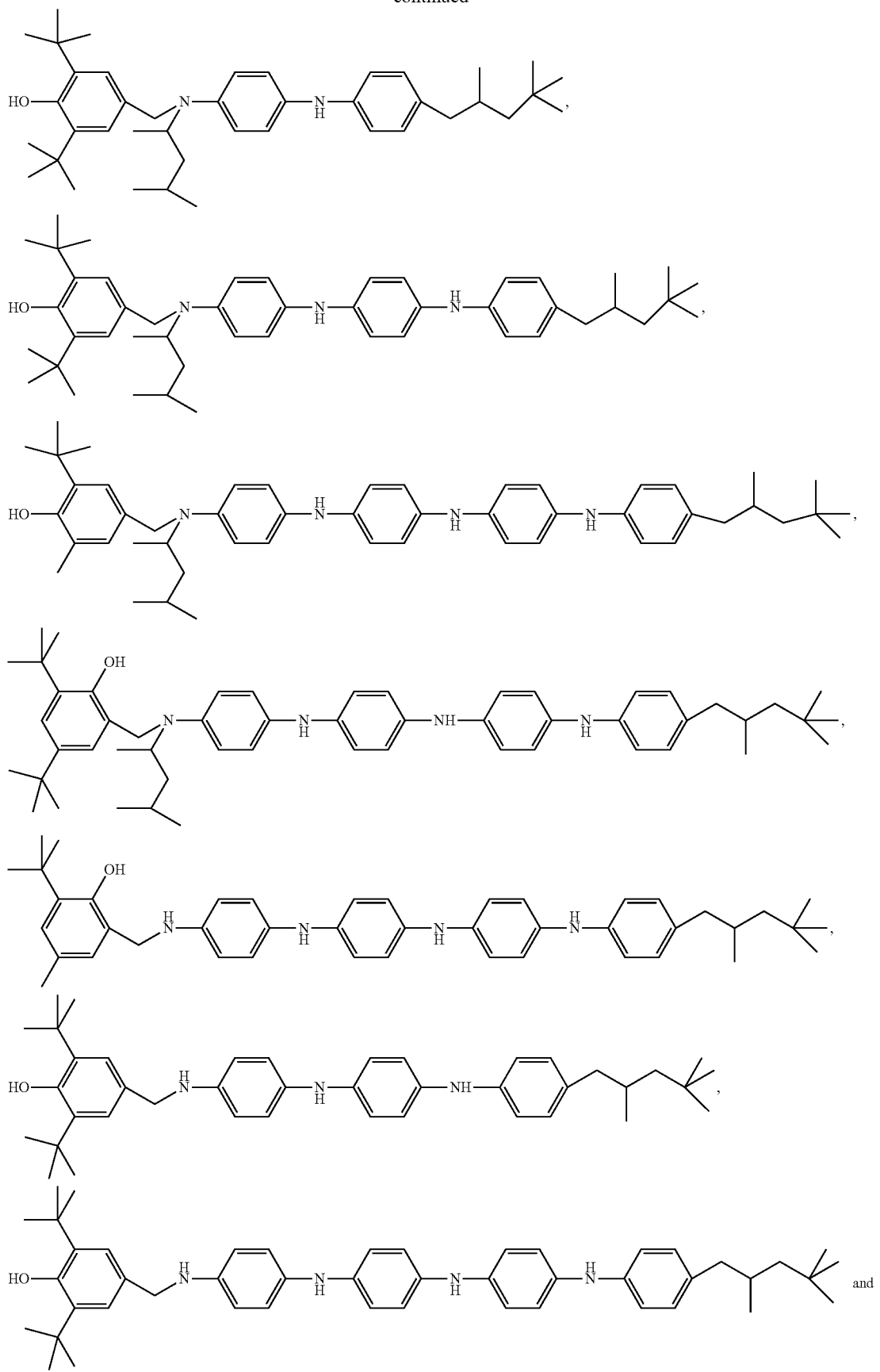

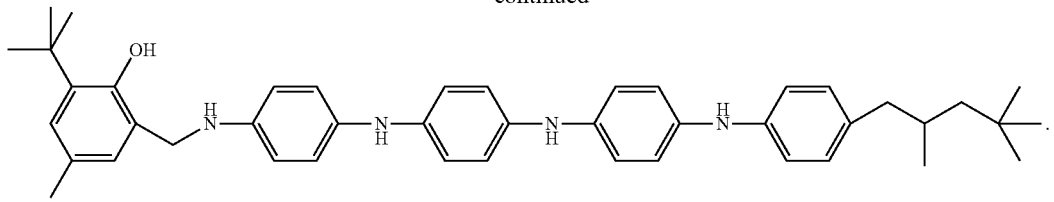

In another embodiment of the present invention for compounds represented by structural formula (III): R" is —H and n is 1 and the compounds are represented by structural formula (VIII):

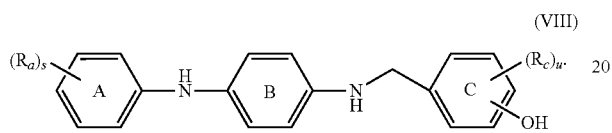

and the remainder of the variables are as described above for structural formula (I), (II) or (III).

In certain embodiments of the present invention the compounds represented by structural formula (III) or (VIII) are represented by the following structural formulas:

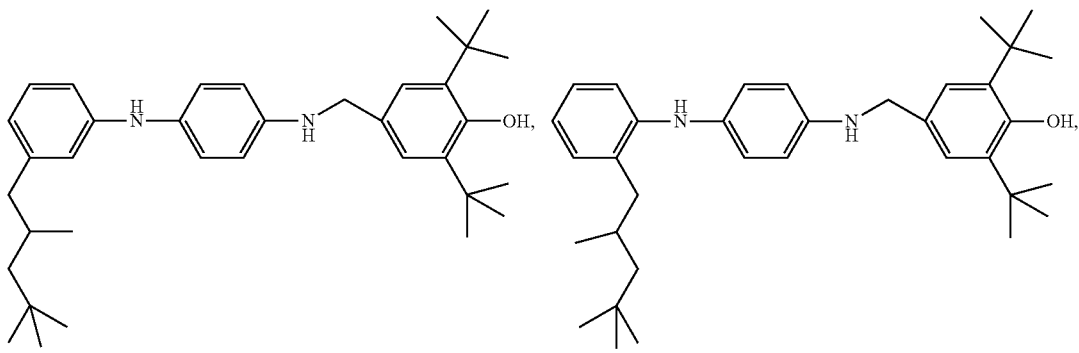

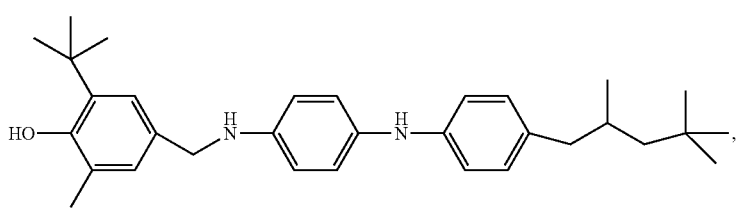

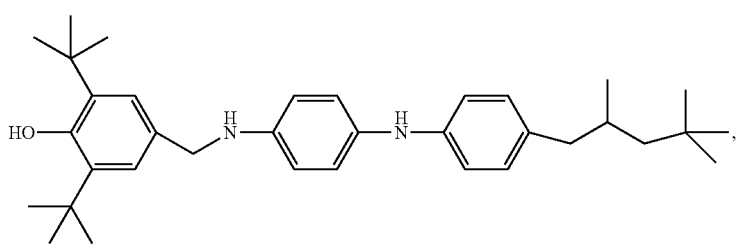

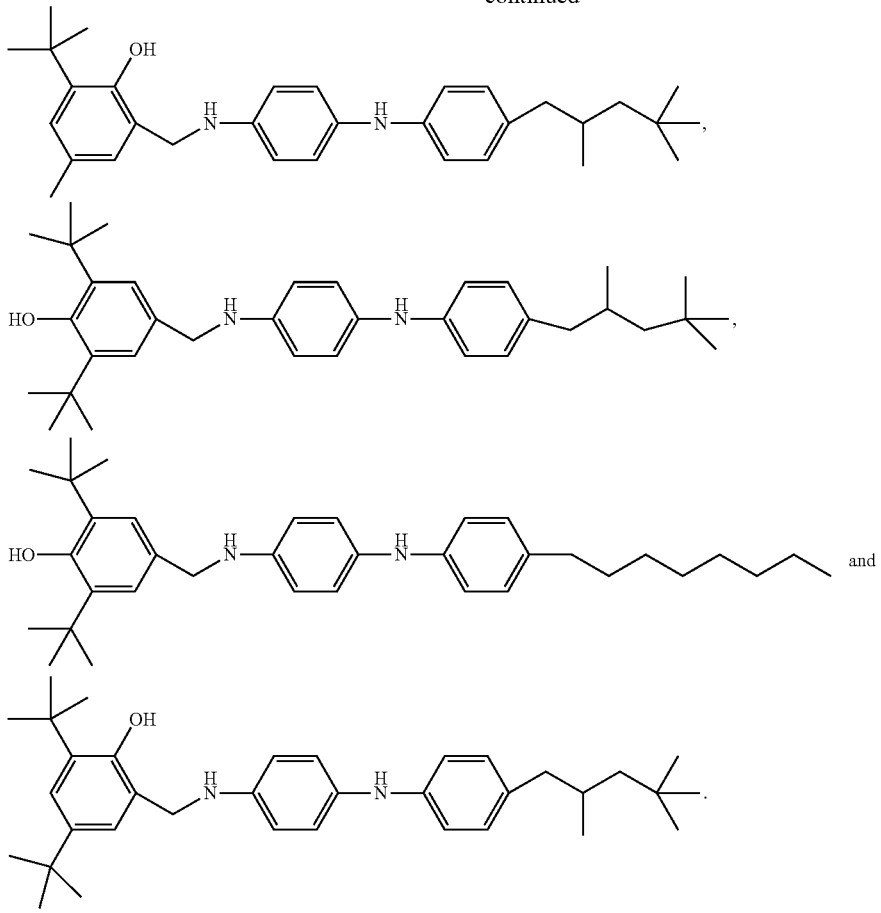

In another embodiment of the present invention for compounds represented by structural formula (III): s is 0 and R" is —H and the compounds are represented by structural formula (IX):

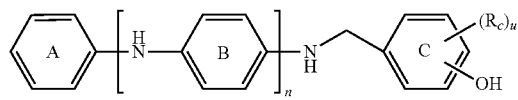

(IX)

and the remainder of the variables are as described above for structural formula (I), (II) or (III).

In certain embodiments of the present invention the compounds represented by structural formula (III) or (IX) are represented by the following structural formulas:

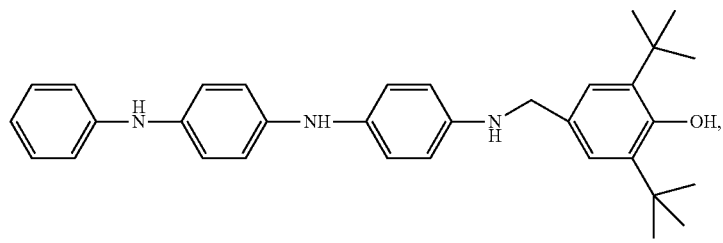

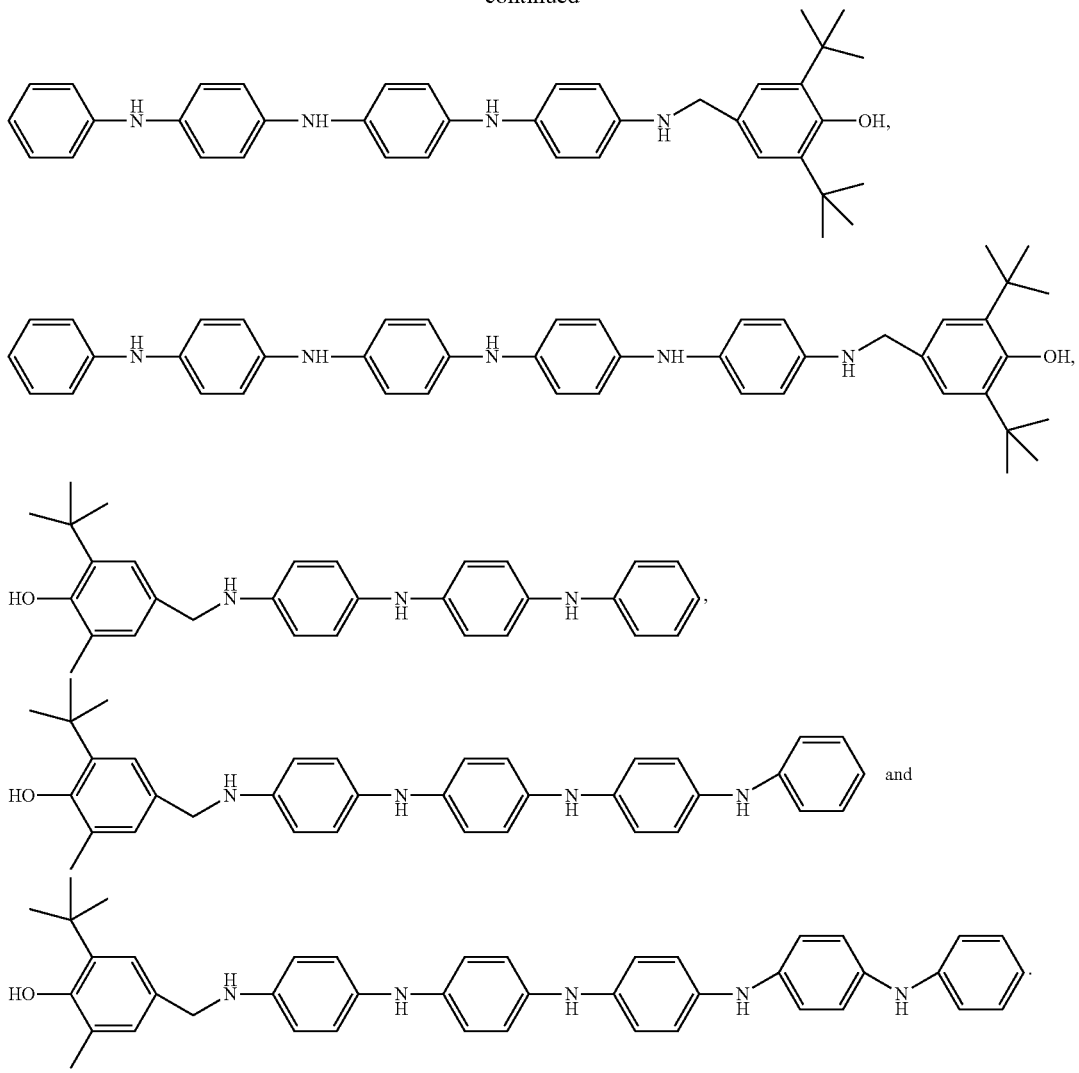

In another embodiment of the present invention for compounds represented by structural formula (III): s is 0 and n is 0 and the compounds are represented by structural formula (X):

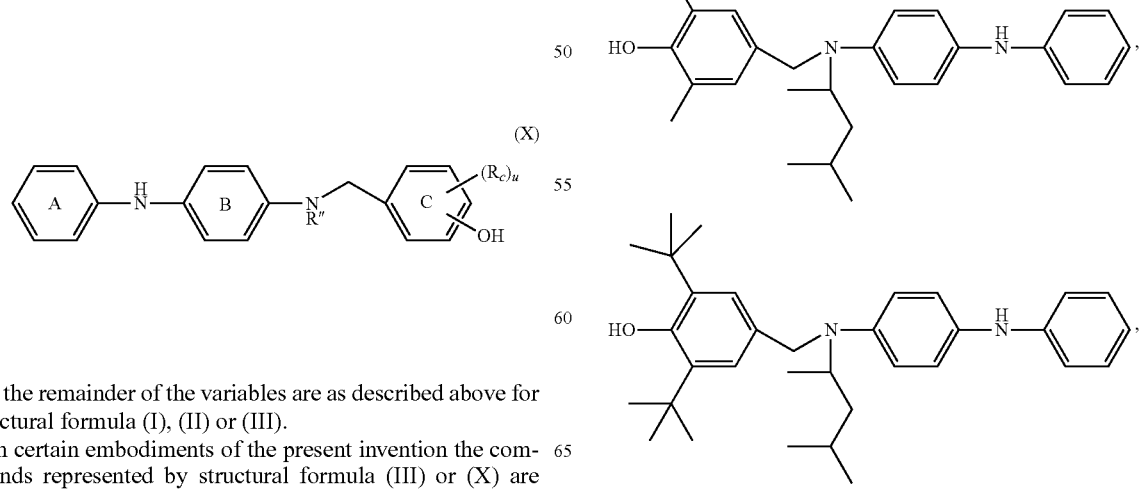

and the remainder of the variables are as described above for structural formula (I), (II) or (III).

In certain embodiments of the present invention the compounds represented by structural formula (III) or (X) are represented by the following structural formulas:

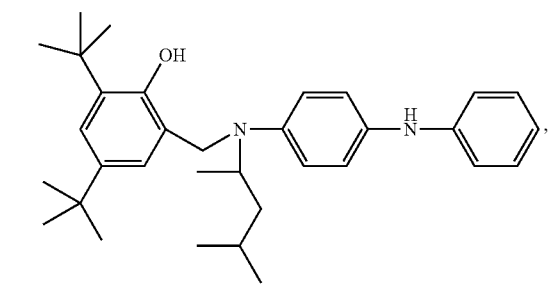
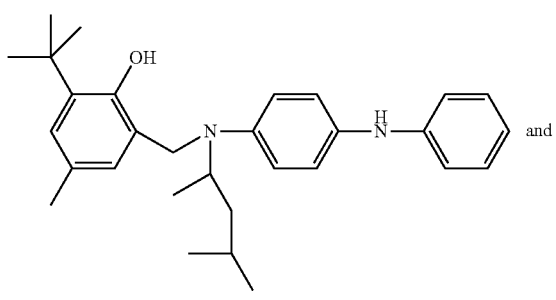
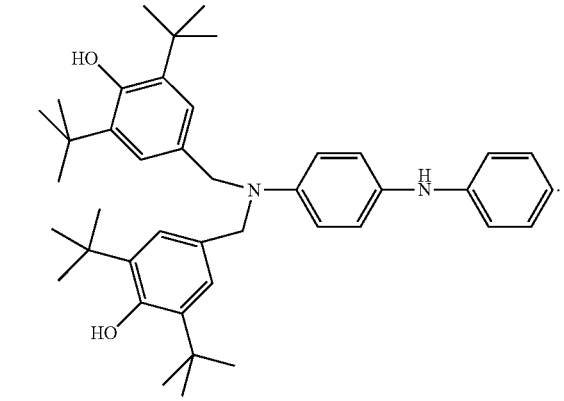
In another embodiment of the present invention the compound is represented by:
I
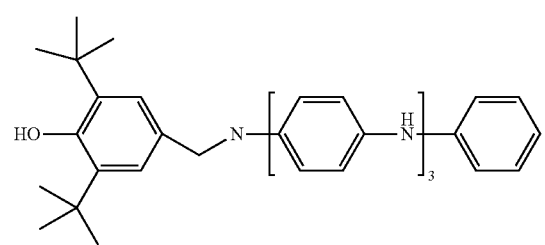
II
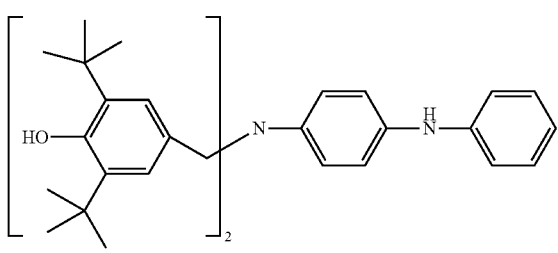
III
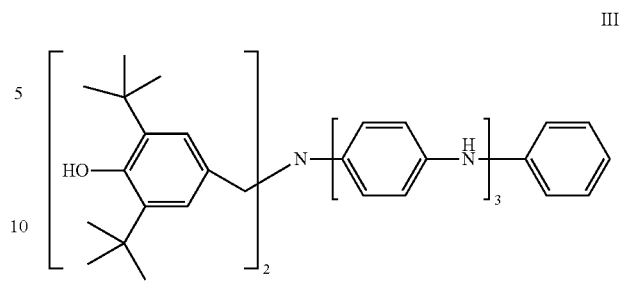
IV
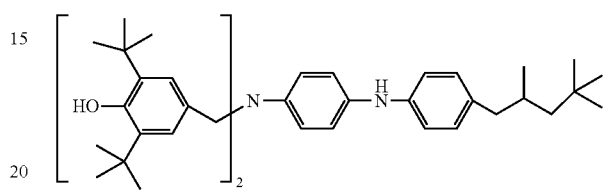
V
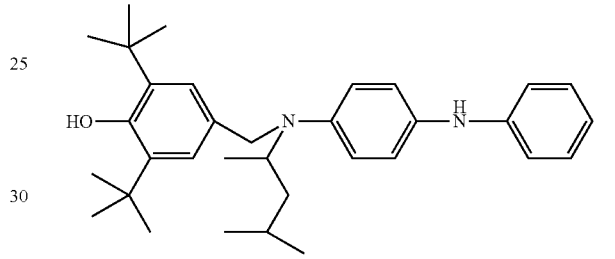
VI
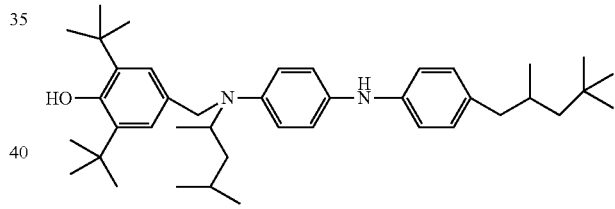
VII
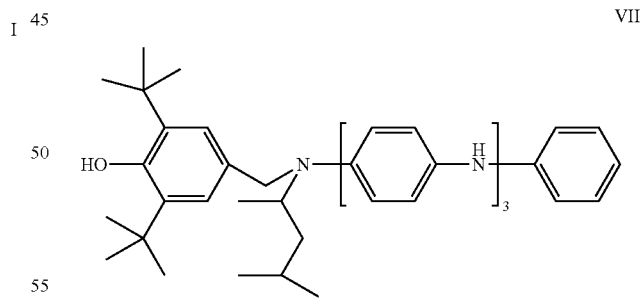
VIII
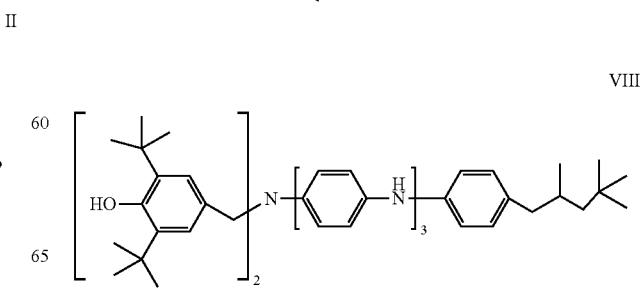

IX
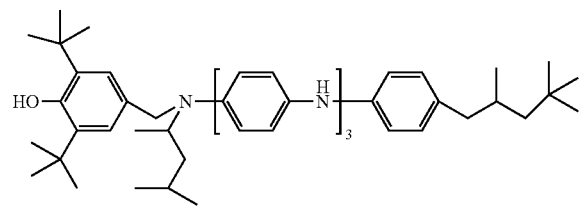
X
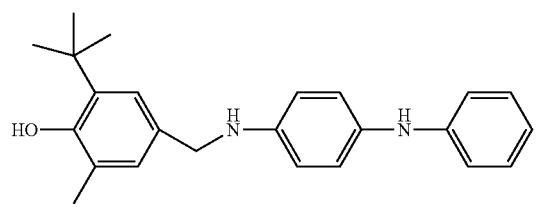
XI
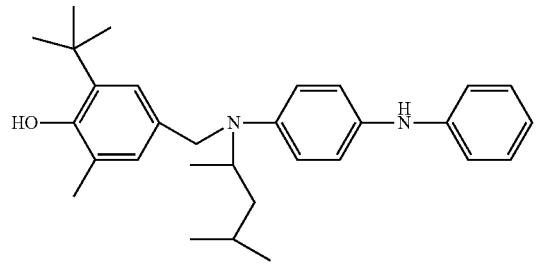
XII
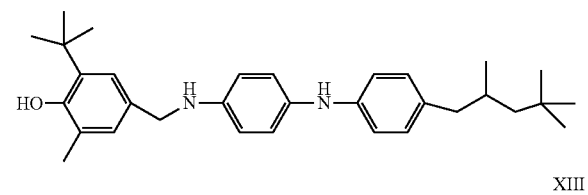
XIII
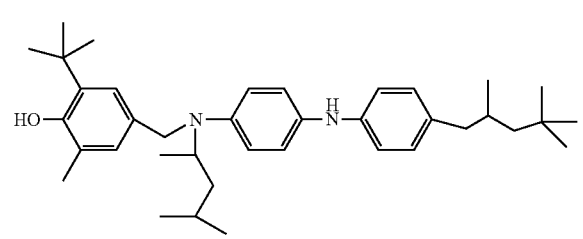
XIV
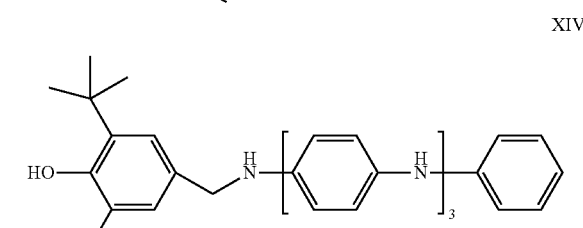
XV
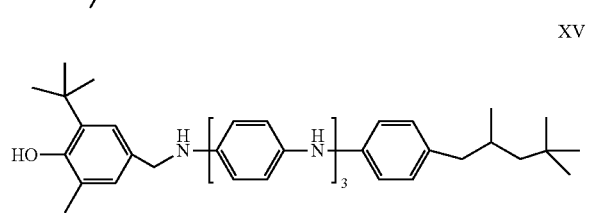
XVI
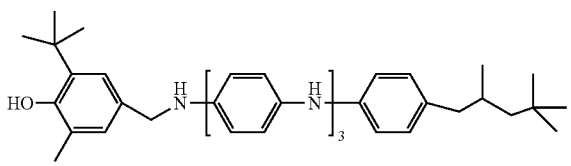
XVII
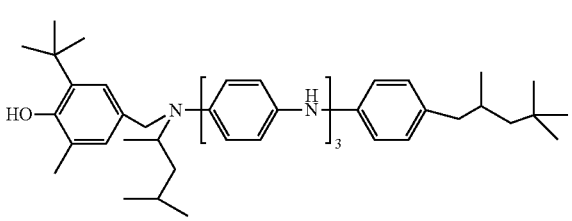
XVIII
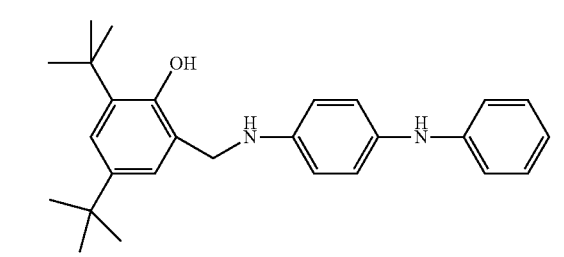
XIX
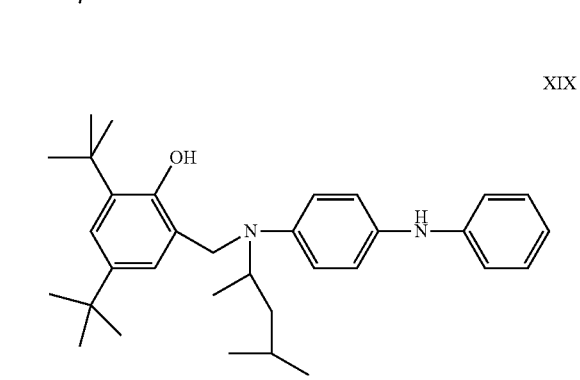
XX
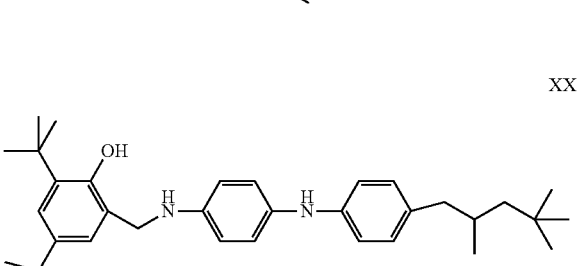
XXI
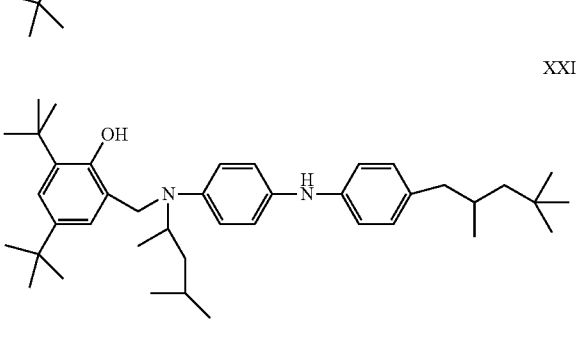

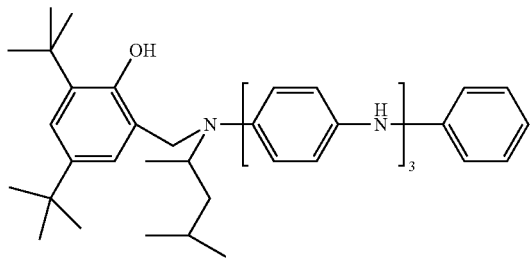

XXII

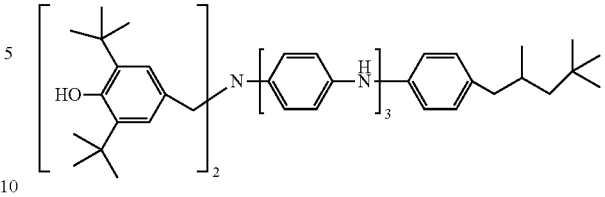

XXVIII

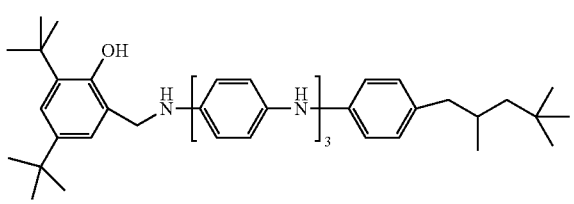

XXIII

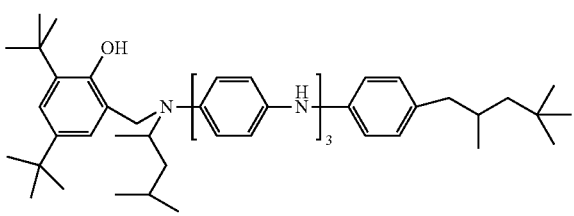

XXIV

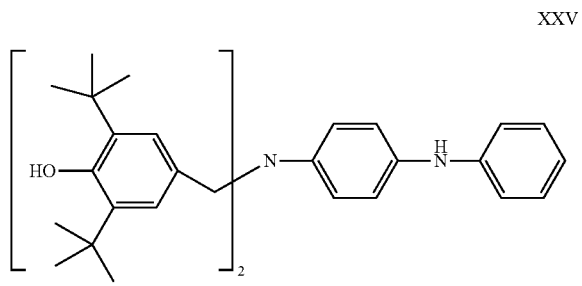

XXV

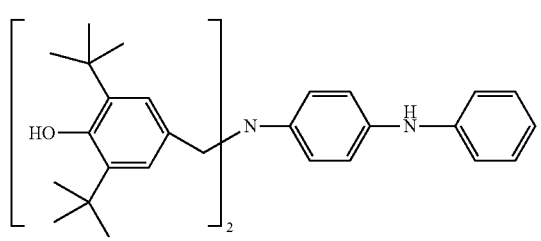

XXVI

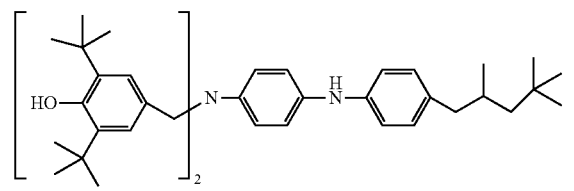

XXVII

The term "alkyl" as used herein means a saturated straight-chain, branched or cyclic hydrocarbon. When straight-chained or branched, an alkyl group is typically C1-C20, more typically C1-C10; when cyclic, an alkyl group is typically C3-C12, more typically C3-C7. Examples of alkyl groups include methyl, ethyl, n-propyl, iso-propyl, n-butyl, sec-butyl and tert-butyl and 1,1-dimethylhexyl.

The term "alkoxy" as used herein is represented by —OR, wherein R is an alkyl group as defined above.

The term "carbonyl" as used herein is represented by —C(=O)R, wherein R is an alkyl group as defined above.

The term "alkoxycarbonyl" as used herein is represented by —C(=O)OR, wherein R is an alkyl group as defined above.

The term "aromatic group" includes carbocyclic aromatic rings and heteroaryl rings. The term "aromatic group" may be used interchangeably with the terms "aryl", "aryl ring" "aromatic ring", "aryl group" and "aromatic group".

Carbocyclic aromatic ring groups have only carbon ring atoms (typically six to fourteen) and include monocyclic aromatic rings such as phenyl and fused polycyclic aromatic ring systems in which a carbocyclic aromatic ring is fused to one or more aromatic rings (carbocyclic aromatic or heteroaromatic). Examples include 1-naphthyl, 2-naphthyl, 1-anthracyl and 2-anthracyl. Also included within the scope of the term "carbocyclic aromatic ring", as it is used herein, is a group in which an aromatic ring is fused to one or more non-aromatic rings (carbocyclic or heterocyclic), such as in an indanyl, phthalimidyl, naphthimidyl, phenanthridinyl, or tetrahydronaphthyl.

The term "heteroaryl", "heteroaromatic", "heteroaryl ring", "heteroaryl group" and "heteroaromatic group", used alone or as part of a larger moiety as in "heteroaralkyl" refers to heteroaromatic ring groups having five to fourteen members, including monocyclic heteroaromatic rings and polycyclic aromatic rings in which a monocyclic aromatic ring is fused to one or more other aromatic ring (carbocyclic or heterocyclic). Heteroaryl groups have one or more ring heteroatoms. Examples of heteroaryl groups include 2-furanyl, 3-furanyl, N-imidazolyl, 2-imidazolyl, 4-imidazolyl, 5-imidazolyl, 3-isoxazolyl, 4-isoxazolyl, 5-isoxazolyl, oxadiazolyl, oxadiazolyl, 2-oxazolyl, 4-oxazolyl, 5-oxazolyl, N-pyrazolyl, 3-pyrazolyl, 4-pyrazolyl, 5-pyrazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-thiazolyl, 4-thiazolyl, 5-thiazolyl, triazolyl, tetrazolyl, 2-thienyl, 3-thienyl, carbazolyl, benzothienyl, benzofuranyl, indolyl, quinolinyl, benzothiazole, benzooxazole, benzimidazolyl, isoquinolinyl and isoindolyl. Also included within the scope of the term "heteroaryl", as it is used herein, is a group in which an aromatic ring is fused to one or more non-aromatic rings (carbocyclic or heterocyclic).

The term non-aromatic heterocyclic group used alone or as part of a larger moiety refers to non-aromatic heterocyclic ring groups having three to fourteen members, including monocyclic heterocyclic rings and polycyclic rings in which a monocyclic ring is fused to one or more other non-aromatic carbocyclic or heterocyclic ring or aromatic ring (carbocyclic or heterocyclic). Heterocyclic groups have one or more ring heteroatoms, and can be saturated or contain one or more units of unsaturation. Examples of heterocyclic groups include piperidinyl, piperizinyl, pyrrolidinyl, pyrazolidinyl, imidazolidinyl, tetrahydroquinolinyl, indolinyl, isoindolinyl, tetrahydrofuranyl, oxazolidinyl, thiazolidinyl, dioxolanyl, dithiolanyl, tetrahydropyranyl, dihydropyranyl, azepanyl and azetidinyl The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heteroaryl or non-aromatic heterocyclic group. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR" (as in N-substituted pyrrolidinyl), wherein R" is a suitable substituent for the nitrogen atom in the ring of a non-aromatic nitrogen-containing heterocyclic group, as defined below. Preferably the nitrogen is unsubstituted.

As used herein the term non-aromatic carbocyclic ring as used alone or as part of a larger moiety refers to a non-aromatic carbon containing ring which can be saturated or contain one or more units of unsaturation, having three to fourteen atoms including monocyclic and polycyclic rings in which the carbocyclic ring can be fused to one or more non-aromatic carbocyclic or heterocyclic rings or one or more aromatic (carbocyclic or heterocyclic) rings An optionally substituted aryl group as defined herein may contain one or more substitutable ring atoms, such as carbon or nitrogen ring atoms. Examples of suitable substituents on a substitutable ring carbon atom of an aryl group include halogen (e.g., —Br, Cl, I and F), —OH, C1-C4 alkyl, C1-C4 haloalkyl, —NO$_2$, C1-C4 alkoxy, C1-C4 haloalkoxy, —CN, —NH$_2$, C1-C4 alkylamino, C1-C4 dialkylamino, —C(O)NH$_2$, —C(O)NH(C1-C4 alkyl), —C(O)(C1-C4 alkyl), —OC(O)(C1-C4 alkyl), —OC(O)(aryl), —OC(O)(substituted aryl), —OC(O)(aralkyl), —OC(O)(substituted aralkyl), —NHC(O)H, —NHC(O)(C1-C4 alkyl), —C(O)N(C1-C4 alkyl)$_2$, —NHC(O)O—(C1-C4 alkyl), —C(O)OH, —C(O)O—(C1-C4 alkyl), —NHC(O)NH$_2$, —NHC(O)NH(C1-C4 alkyl), —NHC(O)N(C1-C4 alkyl)$_2$, —NH—C(=NH)NH$_2$, —SO$_2$NH$_2$—SO$_2$NH(C1-C3alkyl), —SO$_2$N(C1-C3alkyl)$_2$, NHSO$_2$H, NHSO$_2$(C1-C4 alkyl) and optionally substituted aryl. Preferred substituents on aryl groups are as defined throughout the specification. In certain embodiments aryl groups are unsubstituted.

Examples of suitable substituents on a substitutable ring nitrogen atom of an aryl group include C1-C4 alkyl, NH$_2$, C1-C4 alkylamino, C1-C4 dialkylamino, —C(O)NH$_2$, —C(O)NH(C1-C4 alkyl), —C(O)(C1-C4 alkyl), —CO$_2$R, —C(O)C(O)R, —C(O)CH$_3$, —C(O)OH, —C(O)O—(C1-C4 alkyl), —SO$_2$NH$_2$—SO$_2$NH(C1-C3alkyl), —SO$_2$N(C1-C3alkyl)$_2$, NHSO$_2$H, NHSO$_2$(C1-C4 alkyl), —C(=S)NH$_2$, —C(=S)NH(C1-C4 alkyl), —C(=S)N(C1-C4 alkyl)$_2$, —C(=NH)—N(H)$_2$, —C(=NH)—NH(C1-C4 alkyl) and —C(=NH)—N(C1-C4 alkyl)$_2$, An optionally substituted alkyl group or non-aromatic carbocyclic or heterocyclic group as defined herein may contain one or more substituents. Examples of suitable substituents for an alkyl group include those listed above for a substitutable carbon of an aryl and the following: =O, =S, =NNHR, =NN(R)$_2$, =NNHC(O)R, =NNHCO$_2$(alkyl), =NNHSO$_2$(alkyl), =NR, Spiro cycloalkyl group or fused cycloalkyl group. R** in each occurrence, independently is —H or C1-C6 alkyl. Preferred substituents on alkyl groups are as defined throughout the specification. In certain embodiments optionally substituted alkyl groups are unsubstituted.

A "spiro cycloalkyl" group is a cycloalkyl group which shares one ring carbon atom with a carbon atom in an alkylene group or alkyl group, wherein the carbon atom being shared in the alkyl group is not a terminal carbon atom.

In yet another embodiment, the present invention is a method of producing a compound described herein. The method comprises the steps of combining a phenol derivative, an amine and an aldehyde in the presence of a solvent, wherein the phenol derivative comprises at least one unsubstituted ring-carbon atom. Refluxing the combination of the phenol derivative, amine and aldehyde to produce the compound, and isolating the compound.

In certain embodiments of the present invention, the phenol derivative is represented by the following structural formula:

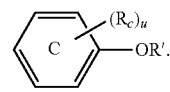

Each $R_c$ is independently an optionally substituted alkyl or optionally substituted alkoxycarbonyl. R' is —H or an optionally substituted alkyl. u is an integer from 1 to 4. Additional values for these variables are as described above. In one embodiment the phenol derivative is selected from:

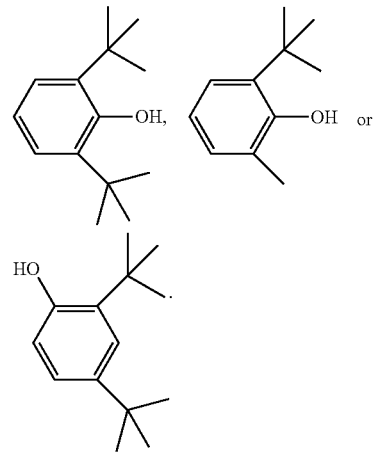

In another embodiment, the amine is represented by the following structural formula:

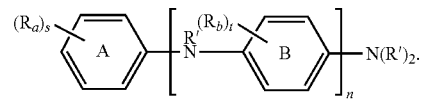

Each $R_a$ is independently an optionally substituted alkyl. Each $R_b$ is independently an optionally substituted alkyl. Each R' is independently —H or an optionally substituted alkyl. n is an integer from 1 to 10. s is an integer from 0 to 5. t is an integer from 0 to 4. Additional values for these variables are as described above.

In certain embodiments the aldehyde used in the methods of the present invention is selected from the group consisting of paraformaldehyde, formaldehyde, butaldehyde and nonaldehyde.

In certain embodiments the solvent used in the methods of the present invention is selected from the group consisting of methanol, butanol, ethanol and toluene.

In certain embodiments of the present invention after combining the amine, aldehyde and phenol derivative in a suitable solvent the combination is refluxed for between 1 and 48 hours, between 6 and 32 hours or between 12 and 24 hours with optional stirring. In certain embodiments the combination is refluxed at a temperature between 20 and 250° C., between 60 and 180° C. or between 100 and 120° C.

In certain embodiments of the present invention equimolar amounts of the phenol derivative and the amine are combined. In certain embodiments of the present invention the phenol derivative and the amine are combined an a 1:0.5, 1:1.2, 1:1.5, 1:1.0 molar ratio of phenol derivative:amine.

The following schemes illustrate particular embodiments of this method:

Scheme A

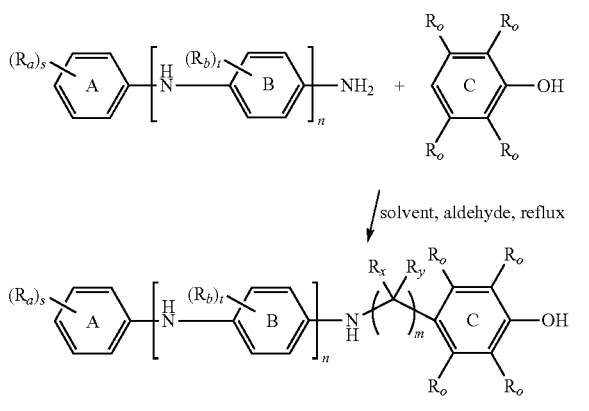

$R_o$ is H, optionally substituted alkyl, or optionally substituted alkoxycarbonyl, all of the remainder of the variables are as described above.

Scheme B

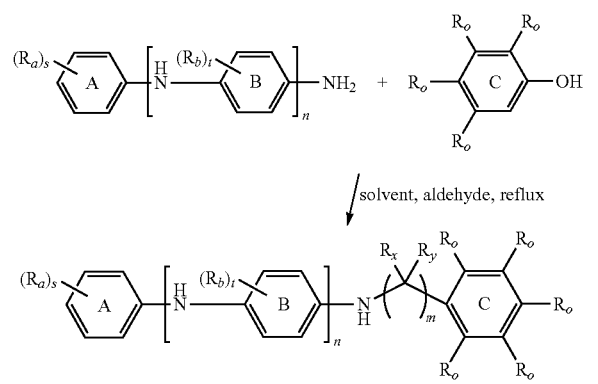

$R_o$ is H, optionally substituted alkyl, or optionally substituted alkoxycarbonyl, all of the remainder of the variables are as described above.

Scheme C

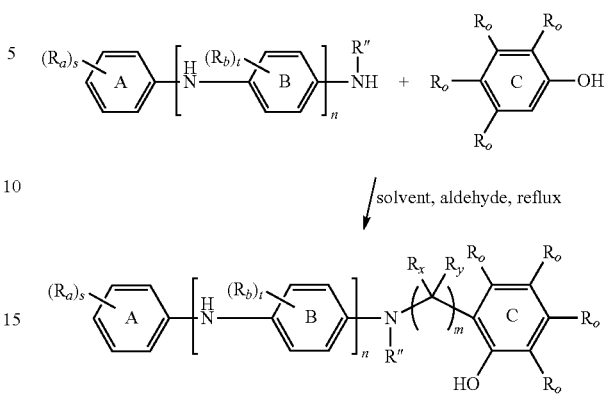

$R_o$ is H, optionally substituted alkyl, or optionally substituted alkoxycarbonyl, all of the remainder of the variables are as described above.

Scheme D

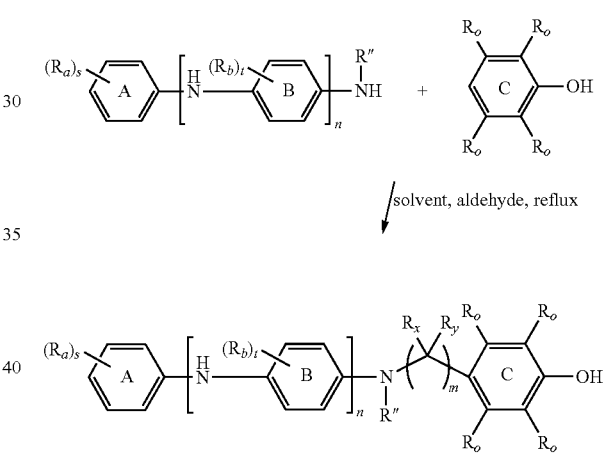

$R_o$ is H, optionally substituted alkyl, or optionally substituted alkoxycarbonyl, all of the remainder of the variables are as described above.

In one embodiment of the present invention the following schemes illustrate the methods described above:

Scheme 3

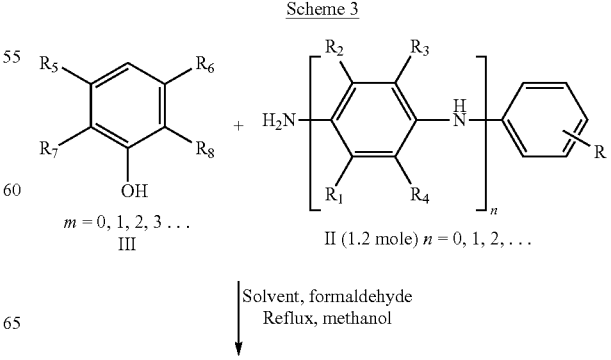

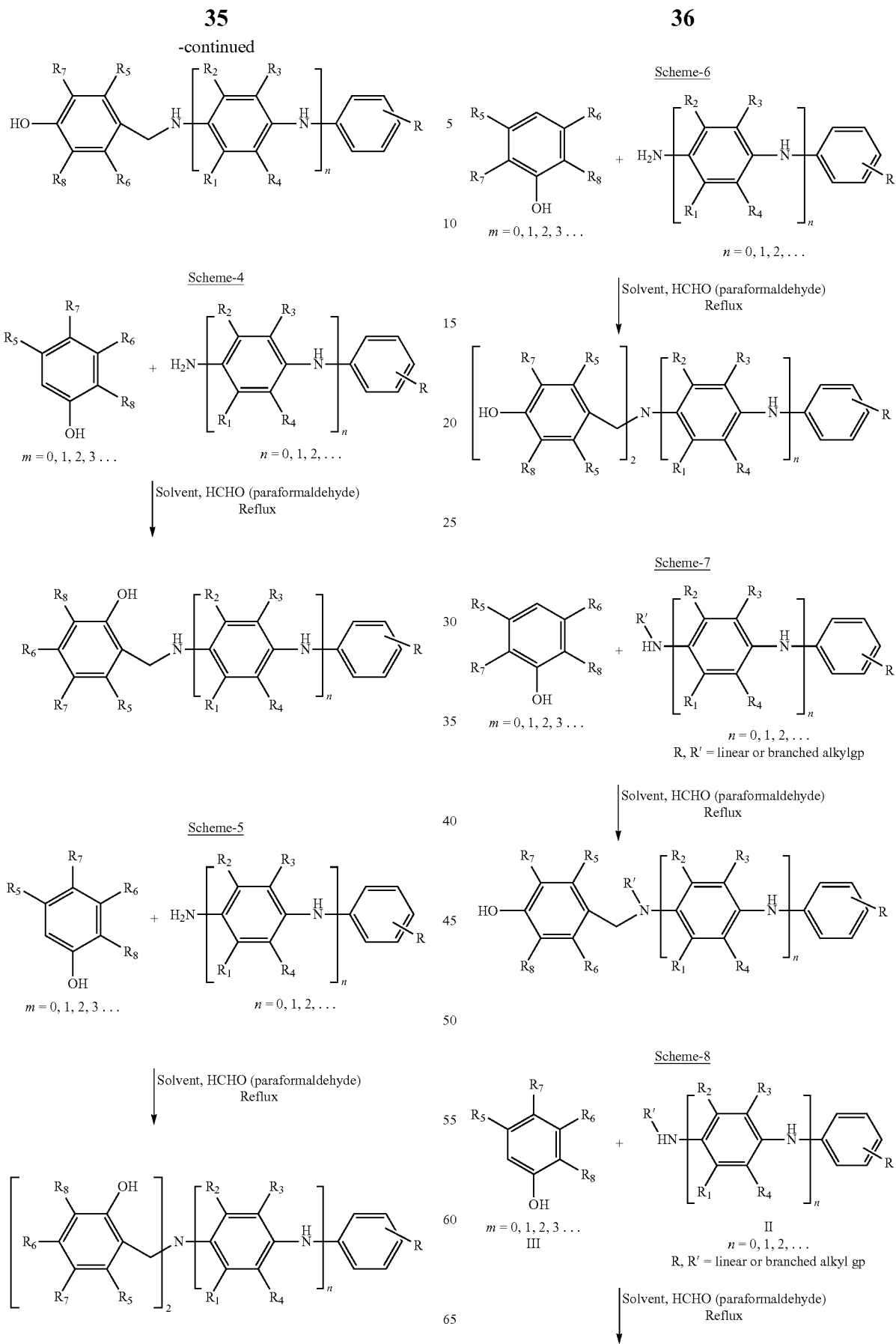

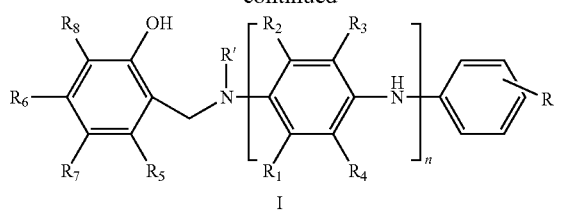

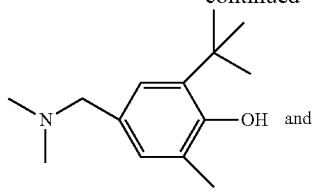

I

The variables R and $R_{1-8}$ described herein correspond to the variables described above for structural formulas (I) through (X) as follows $R_{1-4}$ are equivalent to $R_b$, $R_{5-8}$ are equivalent to $R_c$, R is equivalent to $R_a$, and n and m are the same.

In yet another embodiment the present invention is a method of producing a compound described herein. The method comprises the steps of combining an amino-phenol derivative with an amine in the presence of a solvent. Refluxing the combination to produce the compound, and isolating the compound.

In certain embodiments of the present invention the amino-phenol derivative is represented by the following structural formula:

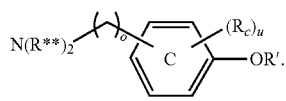

Each $R_c$ is independently an optionally substituted alkyl or an optionally substituted alkoxycarbonyl. R' is —H or an optionally substituted alkyl. R** is an optionally substituted alkyl. o is an integer from 1 to 10. u is an integer from 1 to 4. Additional values for these variables are as described above. In another embodiment the amino-phenol is selected from the group consisting of:

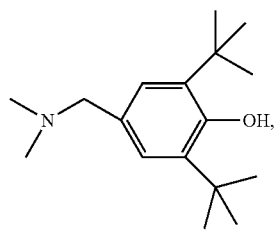

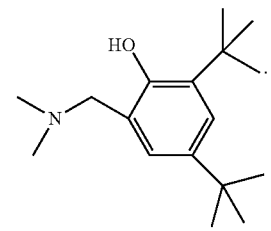

In another embodiment, the amine is represented by the following structural formula:

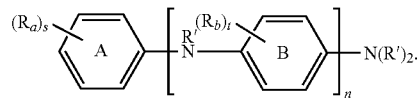

Each $R_a$ is independently an optionally substituted alkyl. Each $R_b$ is independently an optionally substituted alkyl. Each R' is independently —H or an optionally substituted alkyl. In certain embodiments one R' is —H—H and the second R' is —H or an optionally substituted alkyl. n is an integer from 1 to 10. s is an integer from 0 to 5. t is an integer from 0 to 4. Additional values for these variables are as described above.

In certain embodiments, in the methods of the present invention the solvent is selected from the group consisting of toluene, methanol, ethanol and butanol.

In certain other embodiments of the present invention after combining the amine and amino-phenol derivative in a suitable solvent the combination is refluxed at a temperature between 50 and 180° C., between 90 and 130° C., between 100 and 110° C. In certain embodiments, the combination is refluxed for between 1 and 48 hours, between 6 and 36 hours, between 12 and 24 hours or between 18 and 20 hours.

In certain embodiments of the present invention equimolar amounts of the amino-phenol derivative and the amine are combined. In certain embodiments of the present invention the amino-phenol derivative and the amine are combined an a 1:0.5, 1:1.2, 1:1.5, 1:1.0 molar ratio of amino-phenol derivative:amine.

In one embodiment the above method can be conducted in one step and can be conducted without catalyst. The process can be conducted by mixing two starting components in a suitable solvent and heating the reaction mixture to reflux as shown in Scheme E:

Scheme E

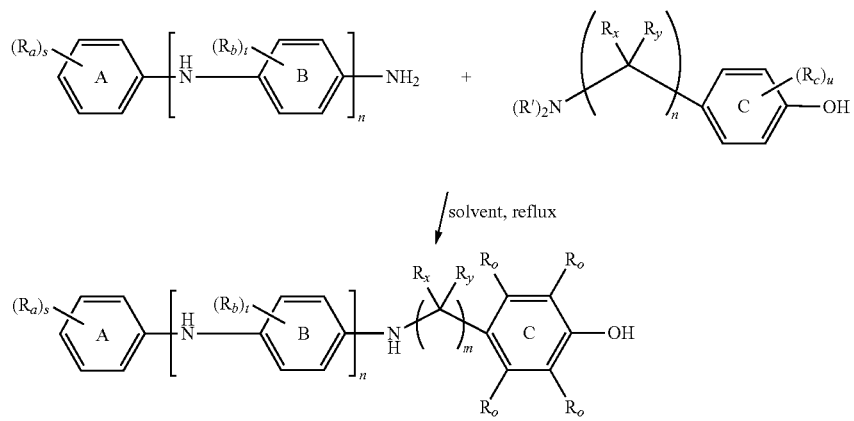

The variables are as described above.

In one embodiment, the above method involves mixing of sterically hindered phenolic acid derivatives, preferably 2,6-di-tert-butyl-4-(dimethyl-aminomethyl)phenol with substituted amines e.g., N-phenyl-1,4-phenylene-diamine in a suitable solvent. The solvent can be a single solvent or mixture of two solvents. In another embodiment, the solvent is toluene.

One embodiment of the present invention is directed to combining equimolar amounts of the starting components, e.g., 2,6-di-tert-butyl-4-(dimethyl-aminomethyl)phenol and N-phenyl-1,4-phenylene-diamine, in toluene and refluxing the reaction mixture at, e.g., 100° C.

In certain embodiment the methods of the present invention are simple, efficient, economical and can be conducted without catalyst.

In certain other embodiments in the methods of the present invention, when solvent is used it can be recycled by separating the solvents from the reaction mixture using distillation.

In one embodiment, the present invention relates to a process or processes for the preparation of macromolecule antioxidants represented by Structural Formula I:

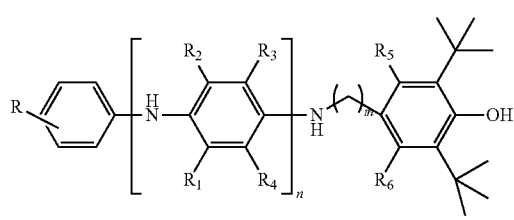

The disclosed synthesis of macromolecules (I) can be conducted in one step and can be conducted without catalyst. The process can be conducted by mixing two starting components in a suitable solvent and heating the reaction mixture to reflux as shown in Scheme 1.

Scheme-1

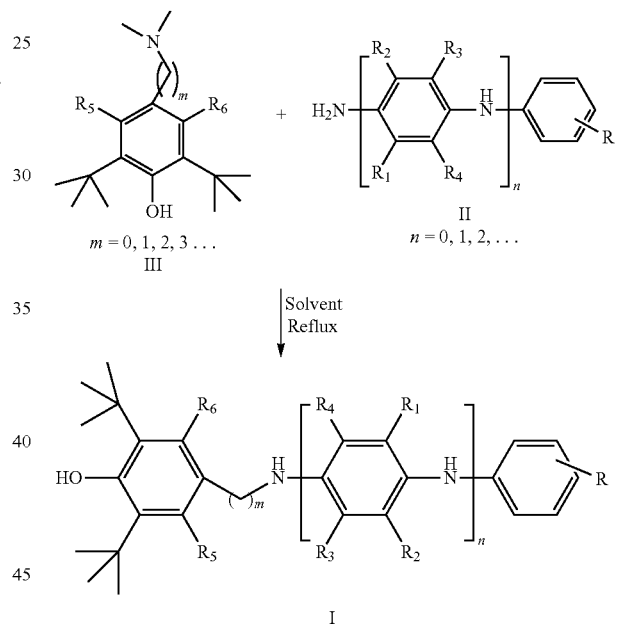

The disclosed process can involve mixing of sterically hindered phenolic acid derivatives, preferably 2,6-di-tert-butyl-4-(dimethyl-aminomethyl)phenol (III) with substituted amines e.g., N-phenyl-1,4-phenylene-diamine (II) in a suitable solvent. The solvent can be a single solvent or mixture of two solvents. The preferred solvent for the process can be toluene. The preferred method can be mixing of equimolar amounts of the starting components, e.g., 2,6-di-tert-butyl-4-(dimethyl-aminomethyl)phenol and N-phenyl-1,4-phenylene-diamine, in toluene and refluxing the reaction mixture at, e.g., 100° C. The disclosed process can be simple, efficient, economical and can be conducted without catalyst. Further, when solvent is used in the process, it can be recycled by separating the solvents from the reaction mixture using distillation Moreover, the above mentioned reaction can also be performed under solvent-less conditions, at 100-180° C., preferably at 110° C.

In yet another embodiment the present invention is a method of producing a compound described herein. The method comprises the steps of combining a phenolic-carbonyl derivative represented by the following structural formula:

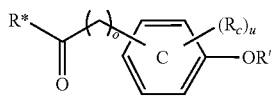

with an amine in the presence of a solvent. Refluxing the combination of phenolic-carbonyl and amine to produce a schiff's base. Reducing the schiff's base with a reducing agent to produce the compound, and isolating the compound. o is an integer from 0 to 10. R* is —H or an optionally substituted alkyl. Additional values for the variables are as described above. In certain embodiments the phenolic carbonyl is selected from the group comprising:

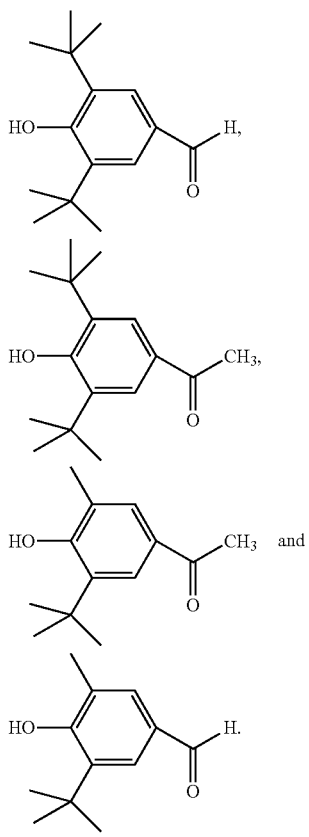

In another embodiment, the amine is represented by the following structural formula:

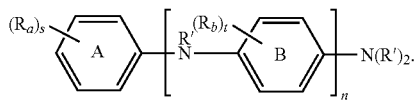

Each $R_a$ is independently an optionally substituted alkyl. Each $R_b$ is independently an optionally substituted alkyl. Each R' is independently —H or an optionally substituted alkyl. n is an integer from 1 to 10. s is an integer from 0 to 5. t is an integer from 0 to 4. Additional values for these variables are as described above.

In certain embodiments of the present invention the solvent is selected from the group consisting of toluene, methanol, ethanol and butanol.

In certain other embodiments of the present invention after combining the amine and phenolic-carbonyl derivative in a suitable solvent the combination is refluxed at a temperature between 50 and 180° C., between 60 and 130° C., between 70 and 110° C. In certain embodiments, the combination is refluxed for between 1 and 48 hours, between 6 and 36 hours, between 12 and 24 hours or between 18 and 20 hours.

In certain embodiments of the present invention equimolar amounts of the phenol-carbonyl derivative and the amine are combined. In certain embodiments of the present invention the amino-phenol derivative and the amine are combined an a 1:0.5, 1:1.2, 1:1.5, 1:1.0 molar ratio of phenol-carbonyl derivative:amine In certain embodiment the reducing agent is selected from the groups consisting of sodium borohydride, sodium cyanoborohydride and lithium aluminum hydride. In certain other embodiments reduction takes place via catalytic hydrogenation. In certain embodiments the catalytic hydrogenation agents are Pd—C or Raney Ni.

In yet another embodiment the present invention is a method of producing a compound described herein. The method comprises the steps of combining a formaldehyde-sodium bisulfite adduct with an amine to produce a methylsulfonate sodium salt in an aqueous media. Followed by the nucleophilic displacement of the sulfonate group with sodium or potassium salt of a phenol derivative, in an aqueous media, to produce the compound, and finally isolating the compound. In certain embodiments the nucleophilic displacement is promoted by base or catalyzed base. In certain embodiments, both combination steps are carried out in an aqueous media.

In certain embodiments the formaldehyde-sodium bisulfite adduct is HO—$CH_2$—$SO_3$Na.

In certain embodiments the methylsulfonate sodium salt is 4-(phenylamino)phenylamino methylsulfonate sodium salt.

In certain embodiments, the phenol derivative and amine are as described above.

In certain embodiments, the aqueous media is water.

In certain embodiments, the base is sodium hydroxide or potassium hydroxide.

In one embodiments of the present invention, the compound is not:

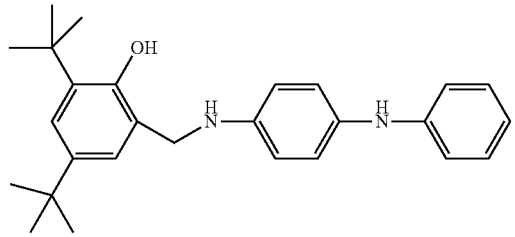

A

The compounds of the present invention can be used as antioxidants to inhibit oxidation of an oxidizable material. Such as, for example to increase the shelf life of an oxidizable material.

The antioxidant compounds of the present invention can be employed to inhibit the oxidation of an oxidizable material, for example by contacting the material with an antioxidant compound made by the methods of the present invention.

For purposes of the present invention, a method of "inhibiting oxidation" is a method that inhibits the propagation of a free radical-mediated process. Free radicals can be generated by heat, light, ionizing radiation, metal ions and some proteins and enzymes. Inhibiting oxidation also includes inhibiting reactions caused by the presence of oxygen, ozone or another compound capable of generating these gases or reactive equivalents of these gases.

As used herein the term "oxidizable material" is any material which is subject to oxidation by free-radicals or oxidative reaction caused by the presence of oxygen, ozone or another compound capable of generating these gases or reactive equivalents thereof. In particular the oxidizable material is a lubricant or a mixture of lubricants.

The shelf life of many materials and substances contained within the materials, such as packaging materials, are enhanced by the presence of the antioxidants of the present invention. The addition of an antioxidant of the present invention to a packaging material is believed to provide additional protection to the product contained inside the package. In addition, the properties of many packaging materials themselves, particularly polymers, are enhanced by the presence of an antioxidant regardless of the application (i.e., not limited to use in packaging). Common examples of packaging materials include paper, cardboard and various plastics and polymers. A packaging material can be coated with an antioxidant (e.g., by spraying the antioxidant or by applying as a thin film coating), blended with or mixed with an antioxidant, or otherwise have an antioxidant present within it. In one example, a thermoplastic such as polyethylene, polypropylene or polystyrene can be melted in the presence of an antioxidant in order to minimize its degradation during the polymer processing.

The lifetime of lubricants, lubricant oils, mixtures thereof and compositions comprising lubricants and lubricant oils in general can be improved by contacting the lubricant, lubricant oil, mixtures thereof or composition comprising the lubricant or lubricant oil or mixtures thereof with compounds of the present invention, as described herein.

As used here, the terms "lubricants" and "lubricant oils" can be used interchangeably. Examples of lubricants suitable for use in the compositions and methods of the present invention include, but are not limited to: i) petroleum based oils (Group I, II and III), ii) synthetic oils (Group IV) and iii) biolubricant oils (vegetable oils such as canola, soybean, corn oil etc.). Group I oils, as defined herein are solvent refined base oils. Group II oils, as defined herein are modern conventional base oils made by hydrocracking and early wax isomerization, or hydroisomerization technologies and have significantly lower levels of impurities than Group I oils. Group III oils, as defined herein are unconventional base oils. Groups I-III differ in impurities, and viscosity index as is shown in Kramer et al. "The Evolution of Base Oil Technology" *Turbine Lubrication in the 21st Century* ASTM STP #1407 W. R. Herguth and T. M. Wayne, Eds., American Society for Testing and Materials, West Conshohocken, Pa., 2001 the entire contents of which are incorporated herein by reference. Group IV oils as defined herein are "synthetic" lubricant oils, including for example, poly-alpha olefins (PAOs). Biolubricants as defined herein are lubricants which contain at least 51% biomaterial (see Scott Fields, Environmental Health Perspectives, volume 111, number 12, September 2003, the entire contents of which are incorporated herein by reference). Other examples of lubricant oils cane be found in Melvyn F. Askew "Biolubricants-Market Data Sheet" IENICA, August 2004 (as part of the IENICA workstream of the IENICA-INFORRM project); Taylor et al. "Engine lubricant Trends Since 1990" paper accepted for publication in the Proceedings I. Mech. E. Part J, Journal of Engineering Tribology, 2005 (Vol. 219 p 1-16); and Desplanches et al. "Formulating Tomorrow's Lubricants" page 49-52 of The Paths to Sustainable Development, part of special report published in October 2003 by Total; the entire contents of each of which are incorporated herein by reference. Biolubricants are often but not necessarily, based on vegetable oils. Vegetable derived, for example, from rapeseed, sunflower, palm and coconut can be used as biolubricants. They can also be synthetic esters which may be partly derived from renewable resources. They can be made from a wider variety of natural sources including solid fats and low grade or waste materials such as tallows. Biolubricants in general offer rapid biodegradability and low environmental toxicity.

As used herein, Group I, II and III oils are petroleum base stock oil. The petroleum industry differentiates their oil based on viscosity index and groups them as Group I, II and III.

In certain embodiments of the present invention, 50% to 20% by weight of the antioxidants of the present invention are added to lubricant oils. In certain other embodiments of the present invention, 10% to 5% by weight of the antioxidants of the present invention are added to lubricant oils. In certain other embodiments of the present invention, 0.1% to 2% by weight of the antioxidants of the present invention are added to lubricant oils. In certain other embodiments of the present invention, 0.001% to 0.5% by weight of the antioxidants of the present invention are added to lubricant oils. This percentage varies depending upon their end application and type of the base oil.

In certain embodiments of the present invention the antioxidants of the present invention are usually added to lubricant oils with stirring at between 0 and 100° C., between 20 and 80° C. or between 40-60° C.

The macromolecules of the present invention can also be made by alkylation of substituted amines, most preferably, N-phenyl-1,4-phenylene-diamine (II) in a suitable solvent by benzyl halides, e.g., preferably 3,5-di-tert-butyl-4-hydroxy benzyl chloride (IV) or 3,5-di-tert-butyl-4-hydroxy benzyl bromide (V) as shown in Scheme 2.

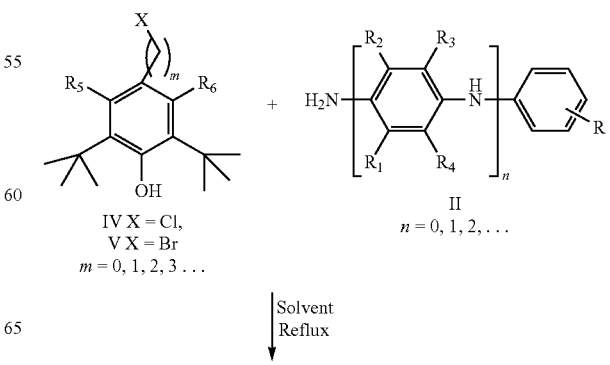

-continued

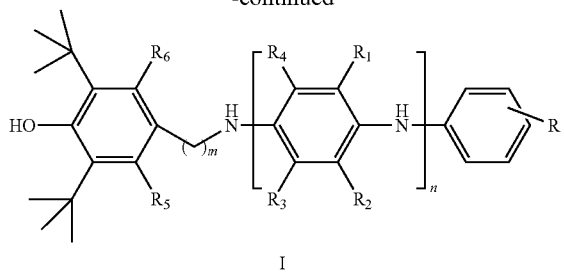

I

EXEMPLIFICATION

Example 1

Illustration of One Pot Process of Making Macromolecules of the Present Invention in Large Scale

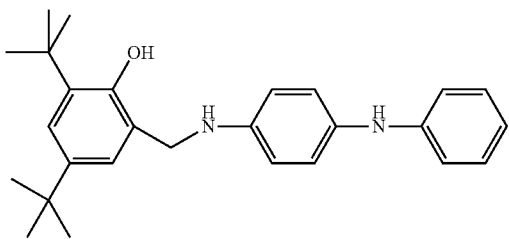

A 2,6-di-tert-butyl-4-(dimethyl-aminomethyl)phenol (26.3 g) and N-Phenyl-1,4-phenylene-diamine (18.4 g) were dissolved in 50 ml toluene. The reaction mixture was refluxed at 100° C. using a Dean Stark apparatus equipped with a condenser. After completion, the solvent was removed by distillation and ice-cold water added and refluxed. The reaction mixture was cooled to room temperature and product was isolated by filtration. The product (A) was characterized using spectroscopic techniques such as high resolution $^1$H NMR, $^{13}$C NMR and FT-IR.

Example 2

Performance of Macromolecules of the Present Invention in Lubricating Oils

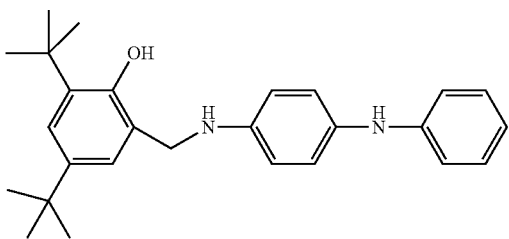

A

Macromolecule A was mixed with oil at 60° C. for 5-15 minutes at 200 ppm in petroleum based group II base stock oil and polyol based Group V base stock oils. It was tested using differential scanning calorimetry (DSC). Its Oxidative Induction Time (OIT) was also compared with commercially used antioxidants 2,6-di-tert-butyl-phenol, Naugalube APAN (PANA) and Vanlube 81 (DODP). FIG. 1 shows the macromolecule A is superior in protecting lubricating oils against oxidation.

Example 3

One Pot Process of Making Compound Having Structure I

I 2,6-di-tert-butyl-4-(dimethyl-aminomethyl)phenol (3 g) and N-Phenyl-1,4-phenylene-diamine (2 g) were dissolved in 100 ml toluene. The reaction mixture was refluxed at 100° C. using a Dean's Stark apparatus equipped with a condenser. The reaction was monitored by thin layer chromatography. After completion, the solvent was removed by distillation and the resultant mixture was purified by column chromatography. The purified compound was characterized by spectroscopic techniques.

Example 4

One Pot Process of Making Compound Having Structure II

II 2,6-di-tert-butyl-4-(dimethyl-aminomethyl)phenol (32 g) and N-Phenyl-1,4-phenylene-diamine (18.4 g) were dissolved in 50 ml toluene. The reaction mixture was refluxed at 100° C. using a Dean's Stark apparatus equipped with a condenser. After completion, the solvent was removed by distillation and ice-cold water added and refluxed. The reaction mixture was cooled to room temperature and product was isolated by filtration. The purified compound was characterized by spectroscopic techniques.

Example 5

One Pot Process of Making Structure V

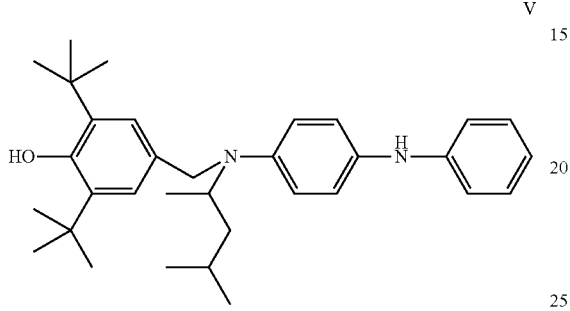

V 2,6-di-tert-butyl phenol (10.3 g), paraformaldehyde (1.8 g) and N-hexyl-Phenyl-1,4-phenylene-diamine (16.08 g) were dissolved in 75 ml methanol. The reaction mixture was refluxed at 70° C. using a Dean's Stark apparatus equipped with a condenser. After completion, the solvent was removed by distillation and ice-cold water added and refluxed. The reaction mixture was cooled to room temperature and product was isolated by filtration. The purified compound was characterized by spectroscopic techniques.

Example 6

One Pot Process of Making Structure X at

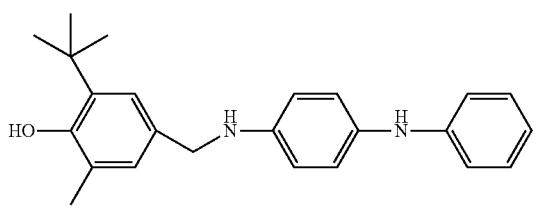

X 2-methyl,6-tert-butyl phenol (16.4 g), paraformaldehyde (3.6 g) and N-Phenyl-1,4-phenylene-diamine (22 g) were dissolved in 50 ml methanol. The reaction mixture was refluxed at 70° C. using a Dean's Stark apparatus equipped with a condenser. After completion, the solvent was removed by distillation and ice-cold water added and refluxed. The reaction mixture was cooled to room temperature and product was isolated by filtration and purified by column chromatography. The purified compound was characterized by spectroscopic techniques.

Example 7

One Pot Process of Making Structure XVIII

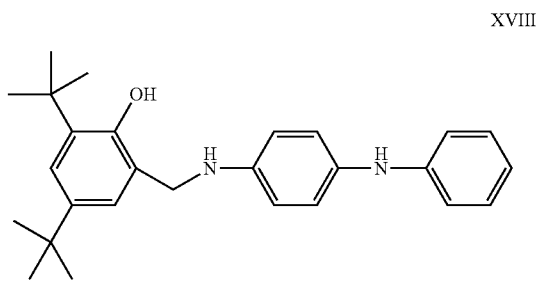 [SMILES: CC(C)(C)c1cc(CNc2ccc(Nc3ccccc3)cc2)c(O)c(C(C)(C)C)c1]

XVIII 2,4-di-tert-butyl phenol (20.6 g), paraformaldehyde (3.6 g) and N-Phenyl-1,4-phenylene-diamine (22 g) were dissolved in 50 ml methanol. The reaction mixture was refluxed at 70° C. using a Dean's Stark apparatus equipped with a condenser. After completion, the solvent was removed by distillation and ice-cold water added and refluxed. The reaction mixture was cooled to room temperature and product was isolated by filtration. The purified compound was characterized by spectroscopic techniques.

Example 8

Performance of Macromolecules of the Present Invention in Lubricating Oils

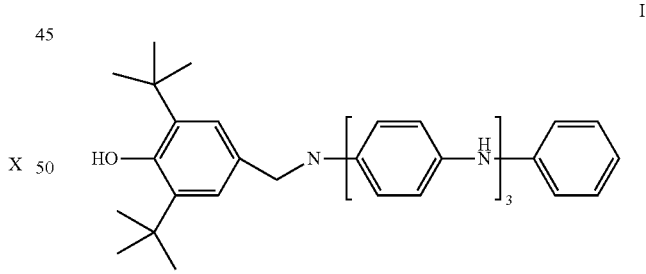

I

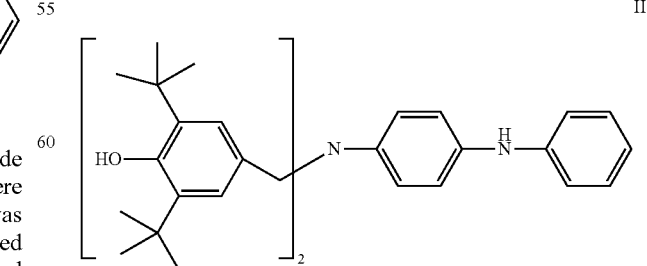

II

-continued

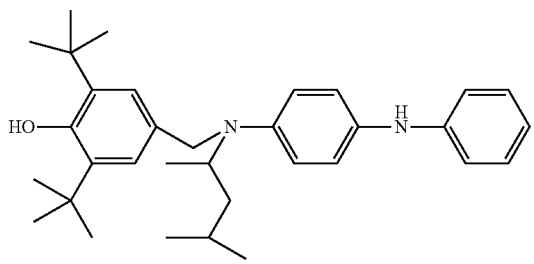

V

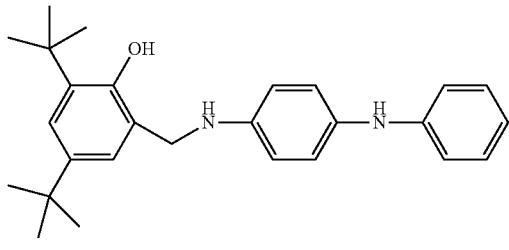

X

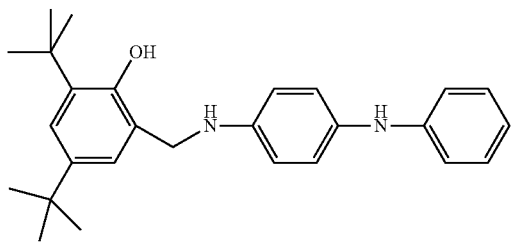

XVIII

A

Figure 2:
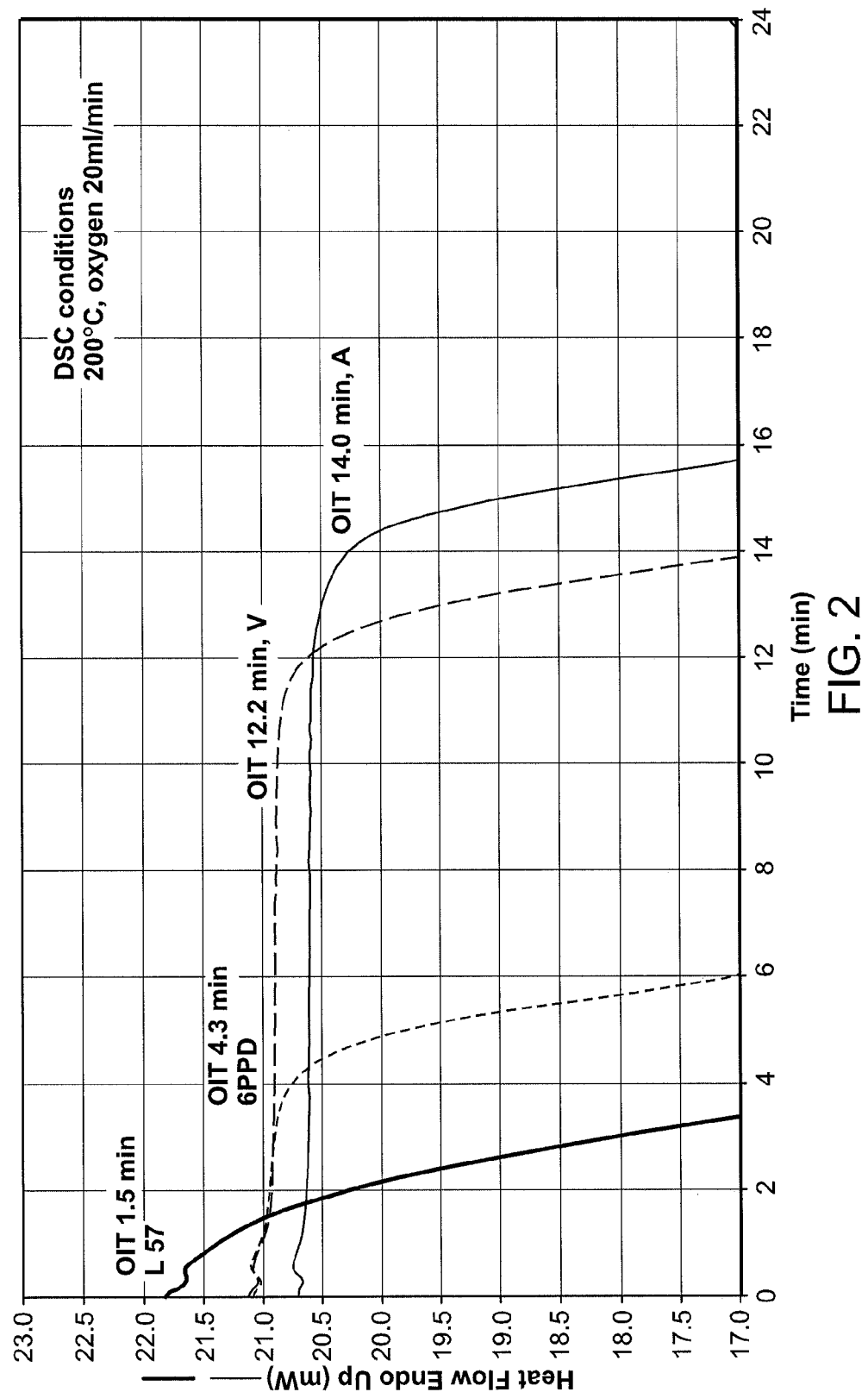
FIG. 2, is a graph of the performance comparison of Oxidative Induction Time (OIT) values of commercial antioxidants versus antioxidants of the present invention in GII base oil at 200 ppm by differential scanning calorimetry (DSC).

Macromolecules V and A were tested for their performance in lubricant oils and polymers. The macromolecules were mixed in oil with stirring at 60° C. for 5-15 mins at 200 ppm in petroleum based Group II base stock and polyol based Group V base stock oils. The performance of these antioxidants were evaluated in lubricant base oil stocks including Group II using the DSC technique for determining their oxidation induction times measured in minutes (OIT) at 200° C. The OITs of the antioxidants having structures V and A were compared with commercial antioxidants [L57: Ciba's Irganox L57, 6PPD: N-hexyl phenyl-1,4-phenylene diamine CAS #793-24-8)]. The results are shown in FIG. 2 which shows the superior performance of V and A.

Macromolecule I, II, X and VIII are mixed in oil with stirring at 60° C. for 5-15 mins at 200 ppm in petroleum based Group II base stock and polyol based Group V base stock oils. The performance of these antioxidants is evaluated in lubricant base oil stocks including Group II using the DSC technique for determining their oxidation induction times measured in minutes (OIT) at 200° C. The OITs of these novel antioxidants having structures I, II, X, XVIII is compared with commercial antioxidants [L57: Ciba's Irganox L57, dioctylated diphenyl amine (DODP, CAS#68411-46-1); 6PPD: N-hexyl phenyl-1,4-phenylene diamine CAS #793-24-8)].

The summary of performance of antioxidants I, II, V, X, XVIII and A and their comparison with commercial antioxidants L 57 and 6PPD in synthetic polyol ester based oil is shown in Table 1. The macromolecules were mixed in oil with stirring at 60° C. for 5-15 mins at 200 ppm in petroleum based Group II base stock and polyol based Group V base stock oils. Table 1, shows the superior performance of these compounds.

TABLE 1

OIT values of various antioxidants in polyester based base stock.

| Antioxidant | OIT @ 200 ppm (min) |
|---|---|
| L 57 | 3 |
| 6PPD | 22 |
| V | 36 |
| A | 37 |
| II | 32 |
| I | 115 |
| X | 28 |
| XVIII | 25 |

OIT values were measured by DSC at 200° C. having Oxygen at 20 ml/min

Figure 3:
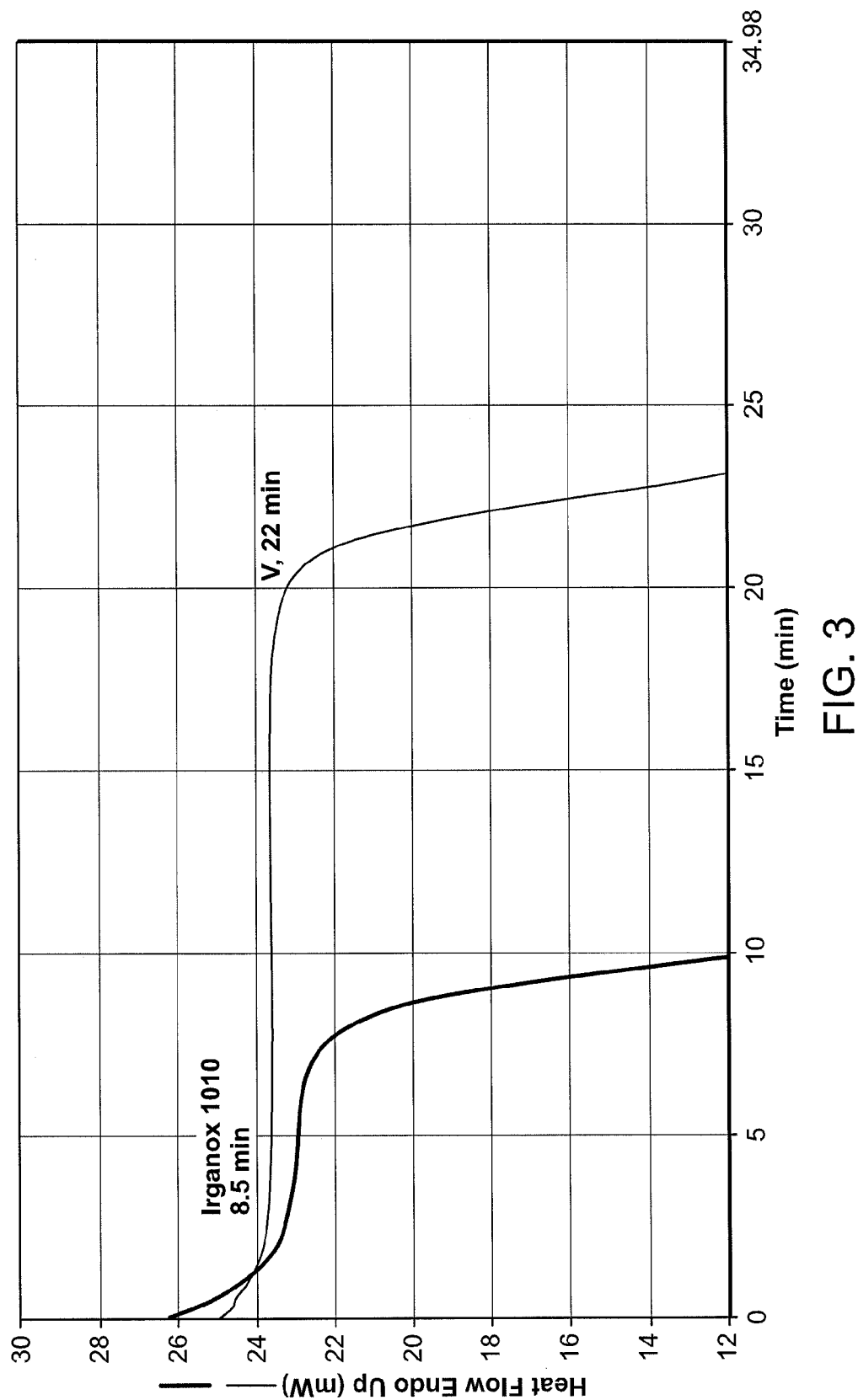
FIG. 3, is a graph of commercial Irganox 1010 versus antioxidants of the present invention in polypropylene at 1000 ppm by DSC.

The performance of antioxidants I, II, V, X, XVIII and A were also evaluated in polyolefins especially in polypropylene (PP) and are compared with the performance of commercially used antioxidant, Irganox 1010 (from Ciba, CAS #6683-19-8). FIG. 3 shows the heat flow as a function time for extruded PP samples containing antioxidants at 1000 ppm level. These samples were prepared under identical processing conditions using a single screw extruder. oxidative induction time (OIT) was determined using ASTM D 3895-95, "Oxidative-Induction Time of Polyolefins by Differential Scanning Calorimetry".

Example 9

Increase Solubility of the Antioxidant V of the Present Invention in Group II Base Stock

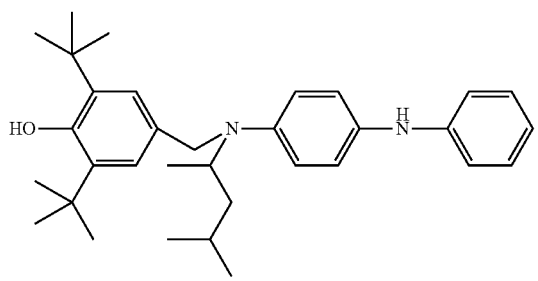

V 10 g of the antioxidant V was added to 90 g of Group II lubricant oil base stock in a beaker. The resultant mixture was stirred for 15 mins in a oil bath maintained at 60° C. to give a homogenous solution. This homogenous solution was used for evaluation. This solubility is much higher than the typical industry standards of 1-2%.

The entire contents of each of the following are incorporated herein by reference.

Provisional Patent Application No. 60/632,893, filed Dec. 3, 2004, Title: Process For The Synthesis Of Polyalkylphenol Antioxidants, by Suizhou Yang, et al;

patent application Ser. No. 11/292,813 filed Dec. 2, 2005, Title: Process For The Synthesis Of Polyalkylphenol Antioxidants, by Suizhou Yang, et al;

Provisional Patent Application No. 60/633,197, filed Dec. 3, 2004, Title: Synthesis Of Sterically Hindered Phenol Based Macromolecular Antioxidants, by Ashish Dhawan, et al.;

patent application Ser. No. 11/293,050; filed Dec. 2, 2005, Title: Synthesis Of Sterically Hindered Phenol Based Macromolecular Antioxidants, by Ashish Dhawan, et al.;

Provisional Patent Application No. 60/633,252, filed Dec. 3, 2004, Title: One Pot Process For Making Polymeric Antioxidants, by Vijayendra Kumar, et al.;

patent application Ser. No. 11/293,049; filed Dec. 2, 2005, Title: One Pot Process For Making Polymeric Antioxidants, by Vijayendra Kumar, et al.;

Provisional Patent Application No. 60/633,196, filed Dec. 3, 2004, Title: Synthesis Of Aniline And Phenol-Based Macromonomers And Corresponding Polymers, by Rajesh Kumar, et al.;

patent application Ser. No. 11/293,844; filed Dec. 2, 2005, Title: Synthesis Of Aniline And Phenol-Based Macromonomers And Corresponding Polymers, by Rajesh Kumar, et al.;

patent application Ser. No. 11/184,724, filed Jul. 19, 2005, Title: Anti-Oxidant Macromonomers And Polymers And Methods Of Making And Using The Same, by Ashok L. Cholli;

patent application Ser. No. 11/184,716, filed Jul. 19, 2005, Title: Anti-Oxidant Macromonomers And Polymers And Methods Of Making And Using The Same, by Ashok L. Cholli;

Provisional Patent Application No. 60/655,169, filed Feb. 22, 2005, Title: Nitrogen And Hindered Phenol Containing Dual Functional Macromolecules Synthesis And Their Antioxidant Performances In Organic Materials, by Rajesh Kumar, et al.

Provisional Patent Application No. 60/655,169, filed Mar. 25, 2005, Title: Alkylated Macromolecular Antioxidants And Methods Of Making, And Using The Same, by Rajesh Kumar, et al.

Provisional Patent Application No. 60/731,125, filed Oct. 27, 2005, Title: Macromolecular Antioxidants And Polymeric Macromolecular Antioxidants, by Ashok L. Cholli, et al.

Provisional Patent Application No. 60/731,021, filed Oct. 27, 2005, Title: Macromolecular Antioxidants Based On Sterically Hindered Phenols And Phosphites, by Ashok L. Cholli, et al.

Provisional patent application No. 60/742,150, filed Dec. 2, 2005, Title: Lubricant Composition, by Kumar, Rajesh, et al.

Provisional Patent Application No. 60/731,325, filed Oct. 27, 2005, Title: Stabilized. Polyolefin Composition, by Kumar, Rajesh, et al.

patent application Ser. No. 11/040,193, filed Jan. 21, 2005, Title: Post-Coupling Synthetic Approach For Polymeric Antioxidants, by Ashok L. Cholli, et al.;

Patent Application No.: PCT/US2005/001948, filed Jan. 21, 2005, Title: Post-Coupling Synthetic Approach For Polymeric Antioxidants, by Ashok L. Cholli et al.;

Patent Application No.: PCT/US2005/001946, filed Jan. 21, 2005, Title: Polymeric Antioxidants, by Ashok L. Cholli, et al.;

Patent Application No.: PCT/US03/10782, filed Apr. 4, 2003, Title: Polymeric Antioxidants, by Ashok L. Cholli, et al.;

patent application Ser. No. 10/761,933, filed Jan. 21, 2004, Title: Polymeric Antioxidants, by Ashish Dhawan, et al.;

patent application Ser. No. 10/408,679, filed Apr. 4, 2003, Title: Polymeric Antioxidants, by Ashok L. Cholli, et al.;

U.S. Pat. No. 6,770,785 B1

U.S. Pat. No. 5,834,544

Neftekhimiya (1981), 21(2): 287-298.

While this invention has been particularly shown and described with references to preferred embodiments thereof, it will be understood by those skilled in the art that various changes in form and details may be made therein without departing from the scope of the invention.

EQUIVALENTS

Those skilled in the art will recognize, or be able to ascertain using no more than routine experimentation, many equivalents to specific embodiments of the invention described specifically herein. Such equivalents are intended to be encompassed in the scope of the following claims.

We claim:

1. A method of inhibiting oxidation in an oxidizable material, comprising combining the oxidizable material with a compound represented by the following structural formula:

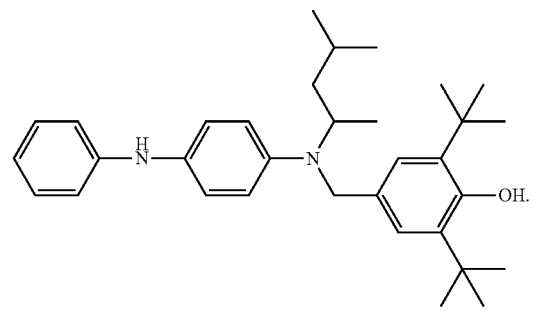 [SMILES: CC(C)CC(C)N(Cc1cc(C(C)(C)C)c(O)c(C(C)(C)C)c1)c1ccc(Nc2ccccc2)cc1]

2. The method of claim 1, wherein the oxidizable material is a lubricant or a mixture of lubricants.

3. The method of claim 2, wherein the lubricant or mixture of lubricants includes petroleum based oils, synthetic oils, and biolubricant oils.

4. The method of claim 3, wherein petroleum based oil include Group I, II and III oils.

5. The method of claim 3, wherein synthetic oils include Group IV oils and Group V oils.

6. The method of claim 3, wherein biolubricants are lubricants which contain at least 51% biomaterial.

7. The method of claim 6, wherein the biolubricants are derived from vegetable oils, solid fats, tallows, and synthetic esters partly derived from renewable resources.

8. The method of claim 1, wherein 50% to 20% by weight of the compound is added to the oxidizable material.

9. The method of claim 1, wherein 10% to 5% by weight of the compound is added to the oxidizable material.

10. The method of claim 1, wherein 0.1% to 2% by weight of the compound is added to the oxidizable material.

11. The method of claim 1, wherein 0.001% to 0.5% by weight of the compound is added to the oxidizable material.

* * * * *